United States Patent
Singh et al.

(10) Patent No.: US 10,004,569 B2
(45) Date of Patent: Jun. 26, 2018

(54) REPOSITIONABLE MEDICAL INSTRUMENT SUPPORT SYSTEMS, DEVICES, AND METHODS

(71) Applicants: Jiwan Steven Singh, Woodvale (AU); Jai Singh, Woodvale (AU)

(72) Inventors: Jiwan Steven Singh, Woodvale (AU); Jai Singh, Woodvale (AU)

( * ) Notice: Subject to any disclaimer, the term of this patent is extended or adjusted under 35 U.S.C. 154(b) by 0 days. days.

(21) Appl. No.: 15/357,749

(22) Filed: Nov. 21, 2016

(65) Prior Publication Data

US 2017/0156817 A1 Jun. 8, 2017

Related U.S. Application Data

(62) Division of application No. 14/387,209, filed as application No. PCT/US2013/037417 on Apr. 19, 2013, now Pat. No. 9,532,837.

(Continued)

(51) Int. Cl.
*A61B 19/00* (2006.01)
*A61B 90/57* (2016.01)
(Continued)

(52) U.S. Cl.
CPC ........ *A61B 90/57* (2016.02); *A61B 17/00234* (2013.01); *A61B 17/42* (2013.01);
(Continued)

(58) Field of Classification Search
CPC ......... A61B 19/20; A61B 19/00; A61B 17/42; A61B 17/56; A61B 17/88; A61B 17/4241
See application file for complete search history.

(56) References Cited

U.S. PATENT DOCUMENTS 2,191,721 A 2/1940 Milarch
2,201,372 A 5/1940 Miller
(Continued)

FOREIGN PATENT DOCUMENTS

AU 773391 5/2004
AU 2011101651 A4 2/2012
(Continued)

OTHER PUBLICATIONS

Cooper Surgical, "Uterine Positioning System™ Facilitates accurate and secure uterine placement," Brochure, revision Dec. 2008, in 5 pages, Trumbull, CT.

(Continued)

*Primary Examiner* — Victor Nguyen
(74) *Attorney, Agent, or Firm* — Knobbe, Martens, Olson & Bear, LLP

(57) ABSTRACT

The disclosure herein provides repositionable medical instrument support systems, devices, and methods. A repositionable medical instrument support system comprises a frame for rigidly connecting the system to a patient support, a ball and socket joint configured to provide three degrees of rotational freedom, a frame mounting arm configured to releasably mount the ball and socket joint to the frame, a sliding joint configured to provide one degree of translational freedom, a connecting arm configured to connect the sliding joint to the ball and socket joint, and a docking member configured to engage a medical instrument to support the medical instrument during a medical procedure.

14 Claims, 19 Drawing Sheets

Related U.S. Application Data

(60) Provisional application No. 61/636,034, filed on Apr. 20, 2012.

(51) Int. Cl.

| | | |
|---|---|---|
| *A61B 17/42* | (2006.01) | |
| *A61B 17/00* | (2006.01) | |
| *A61G 13/10* | (2006.01) | |
| *F16M 11/14* | (2006.01) | |
| *F16M 11/04* | (2006.01) | |

(52) U.S. Cl.
CPC ........ *A61B 17/4241* (2013.01); *A61G 13/101* (2013.01); *F16M 11/043* (2013.01); *F16M 11/14* (2013.01); *A61B 2017/4216* (2013.01); *A61B 2090/571* (2016.02)

(56) References Cited

U.S. PATENT DOCUMENTS

| | | |
|---|---|---|
| 2,400,251 A | 5/1946 | Nagel |
| 2,470,308 A | 5/1949 | Haddican |
| 2,636,598 A | 4/1953 | Hopgood |
| 2,707,471 A | 5/1955 | Koff |
| 3,465,529 A | 9/1969 | Helle |
| 3,926,192 A | 12/1975 | Van Maren |
| 4,045,027 A | 8/1977 | Manska |
| 4,117,847 A | 10/1978 | Clayton |
| 4,207,872 A | 6/1980 | Meiri et al. |
| 4,382,445 A | 5/1983 | Sommers |
| 4,430,076 A | 2/1984 | Harris |
| 4,573,452 A * | 3/1986 | Greenberg ............ A61B 90/50 600/102 |
| 4,840,613 A | 6/1989 | Balbierz |
| 4,859,067 A | 8/1989 | Hoppe et al. |
| 4,863,133 A | 9/1989 | Bonnell |
| 4,863,174 A | 9/1989 | Cummings |
| 4,998,924 A | 3/1991 | Ranford |
| 5,003,146 A | 3/1991 | Alexander |
| 5,052,998 A | 10/1991 | Zimmon |
| 5,112,346 A | 5/1992 | Hiltebrandt et al. |
| 5,138,228 A | 8/1992 | Thomas et al. |
| 5,156,599 A | 10/1992 | Ranford et al. |
| 5,167,614 A | 12/1992 | Tessmann et al. |
| 5,191,888 A | 3/1993 | Palmer et al. |
| 5,205,831 A | 4/1993 | Ryan et al. |
| 5,320,613 A | 6/1994 | Houge et al. |
| 5,338,313 A | 8/1994 | Mollenauer et al. |
| 5,395,331 A | 3/1995 | O'Neill et al. |
| 5,425,739 A | 6/1995 | Jessen |
| 5,472,419 A | 12/1995 | Bacich |
| 5,487,377 A | 1/1996 | Smith et al. |
| 5,501,690 A | 3/1996 | Measamer et al. |
| 5,542,321 A | 8/1996 | Fuca |
| 5,643,285 A | 7/1997 | Rowden et al. |
| 5,741,333 A | 4/1998 | Frid |
| RE35,849 E | 7/1998 | Soehendra |
| 5,792,165 A | 8/1998 | Klieman |
| 5,800,514 A | 9/1998 | Nunez et al. |
| 5,840,077 A | 12/1998 | Rowden |
| 5,876,383 A | 3/1999 | Grooters et al. |
| 5,931,820 A | 8/1999 | Morse |
| 5,947,954 A | 9/1999 | Bonaldo |
| 5,957,423 A | 9/1999 | Kronner |
| 6,004,302 A | 12/1999 | Brierley |
| 6,010,520 A | 1/2000 | Pattison |
| 6,086,606 A | 7/2000 | Knodel et al. |
| 6,096,022 A | 8/2000 | Laymon et al. |
| 6,124,523 A | 9/2000 | Banas et al. |
| 6,203,532 B1 | 3/2001 | Wright |
| 6,254,578 B1 | 7/2001 | Grooters et al. |
| 6,306,146 B1 | 10/2001 | Dinkler |
| 6,371,981 B1 | 4/2002 | Yang et al. |
| 6,423,075 B1 | 7/2002 | Singh et al. |
| 6,516,216 B1 | 2/2003 | Fontenot et al. |
| 6,517,570 B1 | 2/2003 | Lau et al. |
| 6,572,593 B1 | 6/2003 | Daum |
| 6,589,213 B2 | 7/2003 | Reydel |
| 6,692,504 B2 | 2/2004 | Kurz et al. |
| 6,758,834 B2 | 7/2004 | Grooters |
| 6,767,339 B2 | 7/2004 | Reydel |
| 6,811,547 B2 | 11/2004 | Wilkinson |
| 6,893,428 B2 | 5/2005 | Willemstyn |
| 7,044,962 B2 | 5/2006 | Elliott |
| 7,195,641 B2 | 3/2007 | Palmaz et al. |
| 7,338,530 B2 | 3/2008 | Carter et al. |
| 7,811,148 B2 | 10/2010 | Fridrich |
| 7,811,278 B2 | 10/2010 | Knipple, Jr. et al. |
| 7,993,328 B2 | 8/2011 | Whitley |
| 8,042,775 B1 | 10/2011 | Gallegos |
| 8,052,650 B2 | 11/2011 | Young et al. |
| 8,287,517 B2 | 10/2012 | Hanlon et al. |
| 8,298,213 B2 | 10/2012 | Singh |
| 8,495,809 B2 | 7/2013 | Valtchev |
| 8,567,754 B1 | 10/2013 | Gilstad et al. |
| 8,568,423 B2 | 10/2013 | Boebel et al. |
| 8,574,221 B2 | 11/2013 | Deeds |
| 8,603,105 B2 | 12/2013 | Sauer |
| 8,623,070 B2 | 1/2014 | Bales et al. |
| 8,647,325 B2 | 2/2014 | Charlez |
| 8,647,326 B2 | 2/2014 | Solomon et al. |
| 8,647,349 B2 | 2/2014 | Gruber et al. |
| 8,663,239 B2 | 3/2014 | Hess |
| 8,709,362 B2 | 4/2014 | Leventhal et al. |
| 8,740,916 B2 | 6/2014 | Blair et al. |
| 8,770,200 B2 | 7/2014 | Ahluwalia |
| 8,876,800 B2 | 11/2014 | Kaufmann et al. |
| 8,876,886 B2 | 11/2014 | Kaufmann et al. |
| 9,101,390 B2 | 8/2015 | Singh et al. |
| 9,451,985 B2 | 9/2016 | Singh et al. |
| 9,532,837 B2 | 1/2017 | Singh et al. |
| 2002/0095160 A1 | 7/2002 | Bonutti |
| 2002/0120252 A1* | 8/2002 | Brock ................ A61B 17/0469 606/1 |
| 2003/0010088 A1 | 1/2003 | Tomisawa |
| 2004/0097961 A1 | 5/2004 | Burbank et al. |
| 2004/0204720 A1 | 10/2004 | Harrington et al. |
| 2004/0236285 A1 | 11/2004 | Fisher et al. |
| 2005/0085827 A1 | 4/2005 | G. et al. |
| 2005/0277948 A1 | 12/2005 | Cedars et al. |
| 2007/0135819 A1 | 6/2007 | Spiritos et al. |
| 2008/0039865 A1 | 2/2008 | Shaher et al. |
| 2008/0154244 A1 | 6/2008 | Singh |
| 2009/0048609 A1 | 2/2009 | Atiomo et al. |
| 2009/0062839 A1 | 3/2009 | Kurrus |
| 2010/0160928 A1 | 6/2010 | Navas |
| 2010/0274260 A1 | 10/2010 | D'Arpiany et al. |
| 2011/0282368 A1 | 11/2011 | Swayze et al. |
| 2011/0306829 A1 | 12/2011 | Sharp et al. |
| 2012/0109124 A1 | 5/2012 | Morozov |
| 2012/0143209 A1 | 6/2012 | Brecheen et al. |
| 2012/0143210 A1 | 6/2012 | Brecheen et al. |
| 2013/0066328 A1 | 3/2013 | Singh et al. |
| 2013/0197536 A1 | 8/2013 | Singh et al. |
| 2014/0100595 A1 | 4/2014 | Morgenstern Lopez et al. |
| 2014/0135587 A1 | 5/2014 | Hess |
| 2014/0276916 A1 | 9/2014 | Ahluwalia et al. |
| 2014/0303641 A1 | 10/2014 | Boebel et al. |
| 2016/0081717 A1 | 3/2016 | Singh et al. |

FOREIGN PATENT DOCUMENTS

| | | |
|---|---|---|
| AU | 2007335226 | 9/2012 |
| CA | 2778976 | 8/2012 |
| CN | 201005764 | 1/2008 |
| DE | 10208508 | 1/2003 |
| EP | 0400458 | 12/1990 |
| JP | 2006-122674 | 10/2005 |
| JP | 2009-273891 | 11/2009 |
| JP | 2011-104399 | 6/2011 |
| KR | 10-2001-0052102 A | 6/2001 |
| WO | WO 2008/074054 | 6/2008 |
| WO | WO 2008/136024 | 9/2008 |
| WO | WO 2010/151429 | 12/2010 |

(56) References Cited

FOREIGN PATENT DOCUMENTS

| WO | WO 2011/140604 | 9/2011 |
|---|---|---|
| WO | WO 2012/135893 | 10/2012 |
| WO | WO 2013/159019 | 10/2013 |
| WO | WO 2014/047554 | 3/2014 |

OTHER PUBLICATIONS

Surgitools, Instructions for Use: Singh MultiGuide ARC, Apr. 30, 2013.
International Preliminary Report on Patentability for PCT Application No. PCT/AU2012/000332, dated Feb. 27, 2013.
International Search Report and Written Opinion, International Application No. PCT/AU2012/000332, International Filing Date, Mar. 30, 2012, dated May 17, 2012.
International Search Report and Written Opinion for PCT Application No. PCT/US2013/061180, dated Dec. 17, 2013.
International Search Report and Written Opinion for PCT/US2013/037417, dated Jul. 29, 2013.
Ob.Gyn.News, "Kronner non-Pneumatic Scope/Instrument Holder for laparoscopic and other endoscopic surgery," updated Mar. 16, 2013, in 2 pages, product.zone.obgynnews.com.
R. Kronner, MD FACS, "The Kronner Side-Kick: A Perineal Instrument Holder," manual in 13 pages, Kronner Medical, Roseburg, Oregon.
Stryker, "Give Yourself a Hand," Stryker Endoscopy Brochure, in 2 pages, 2006, Stryker, San Jose, CA.
SecuFix Uterus Manipulator, 4 pages, www.richard-wolf.com. The "publication date" of this reference is not readily available. Applicant requests that the Examiner review the reference as prior art. Applicant reserves the right to disqualify the reference as prior art if needed.

\* cited by examiner

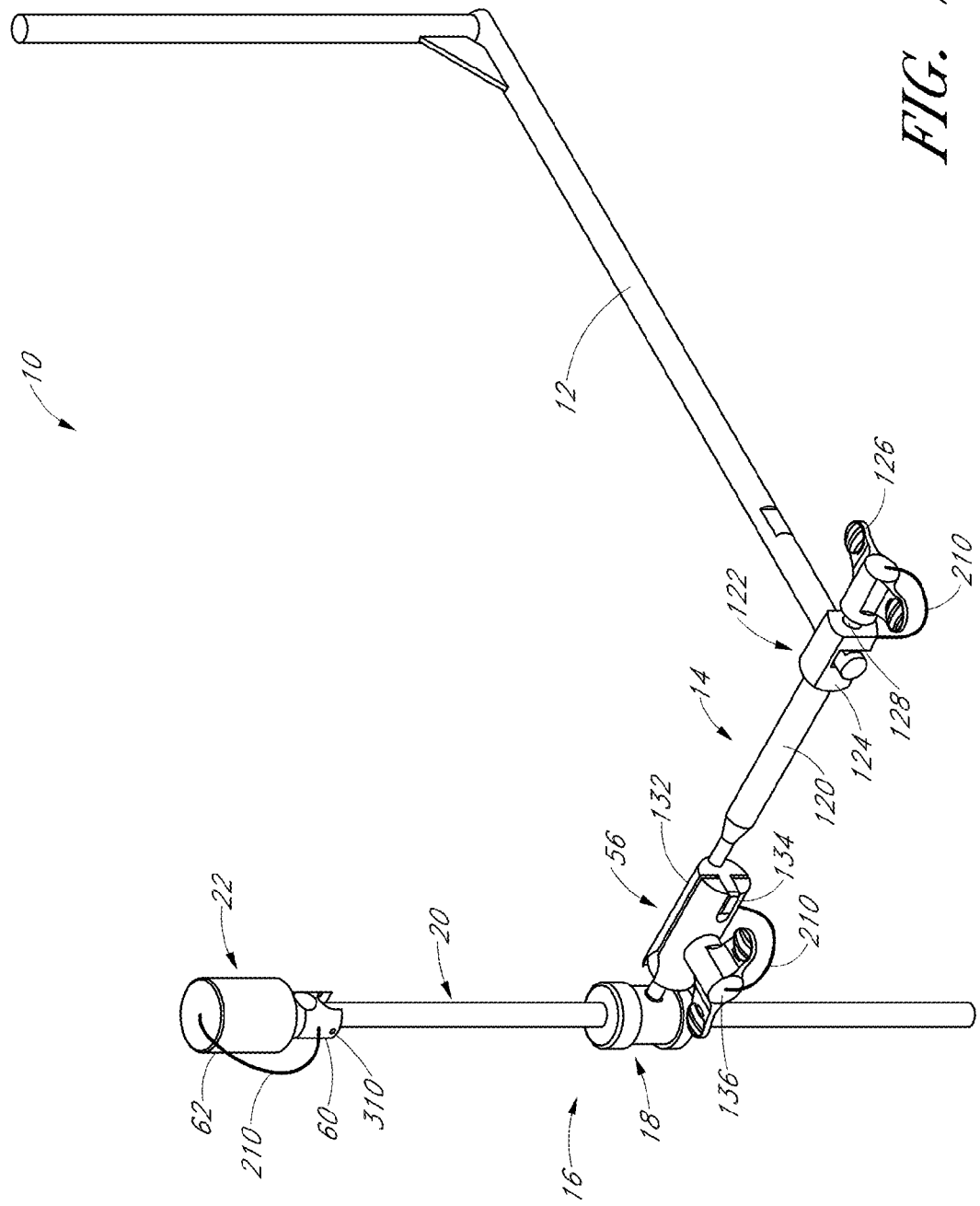

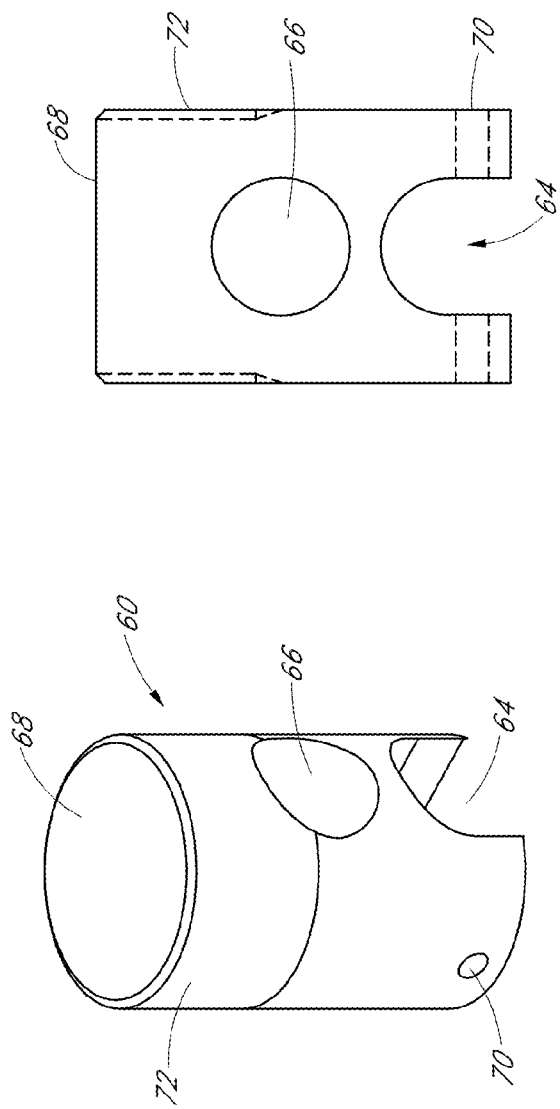
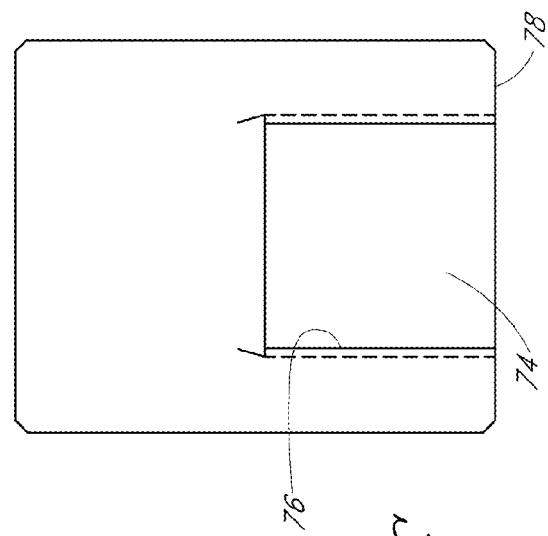
FIG. 3A
FIG. 3B
FIG. 3C

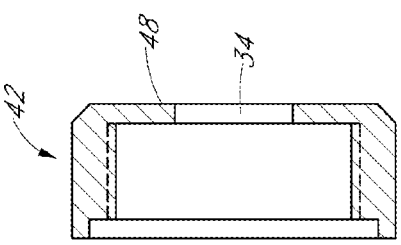
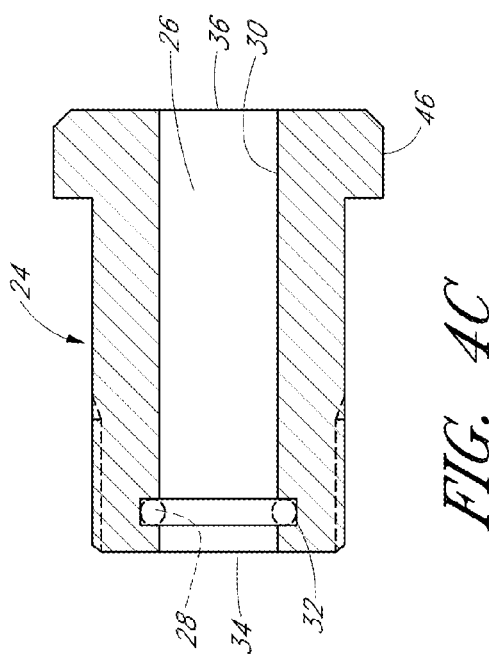
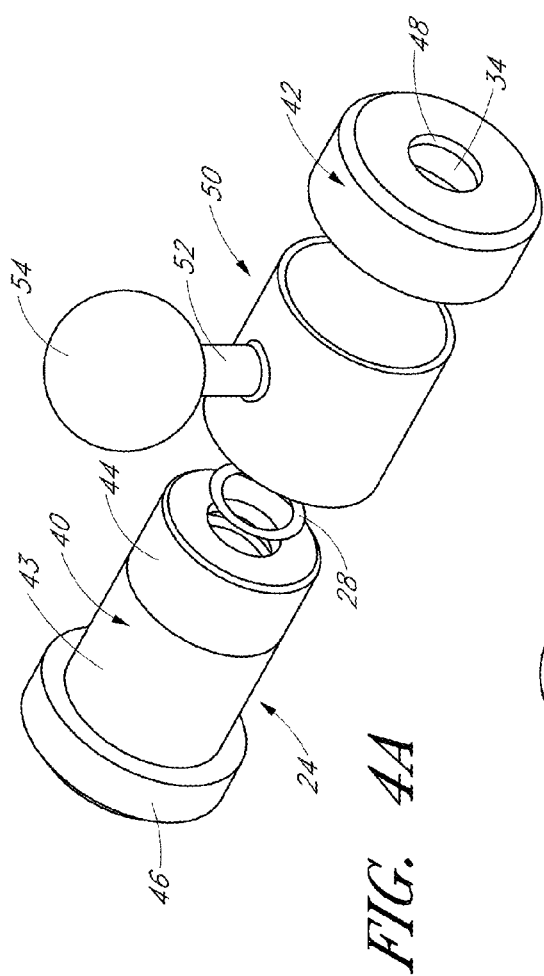
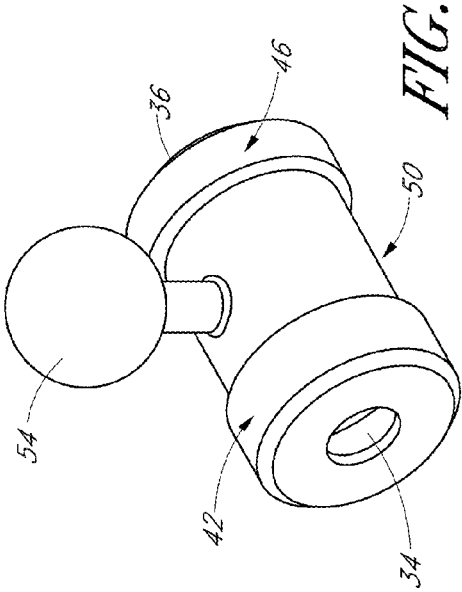

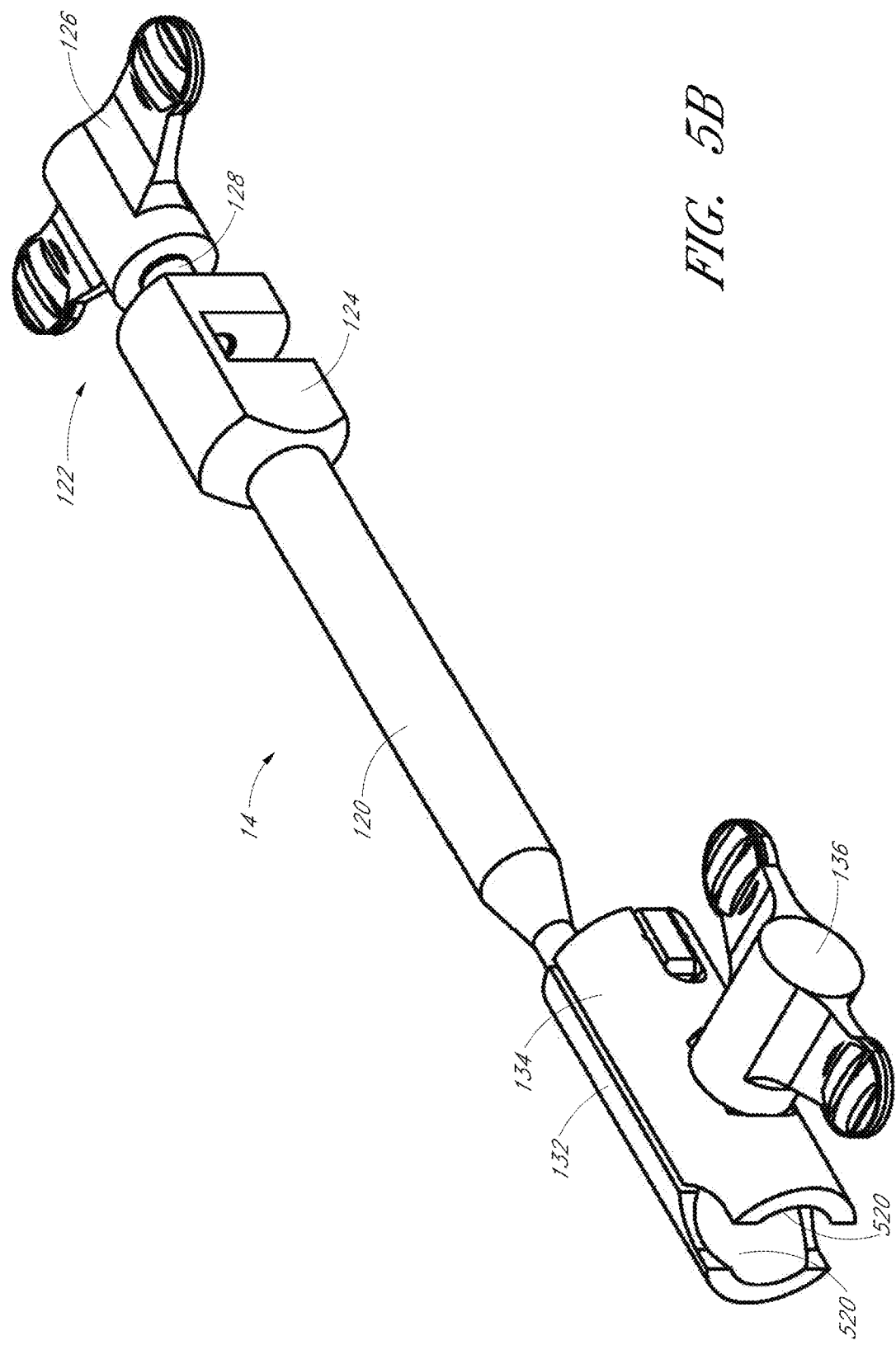

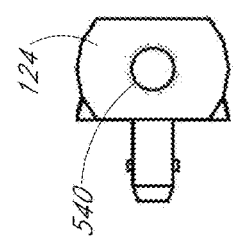
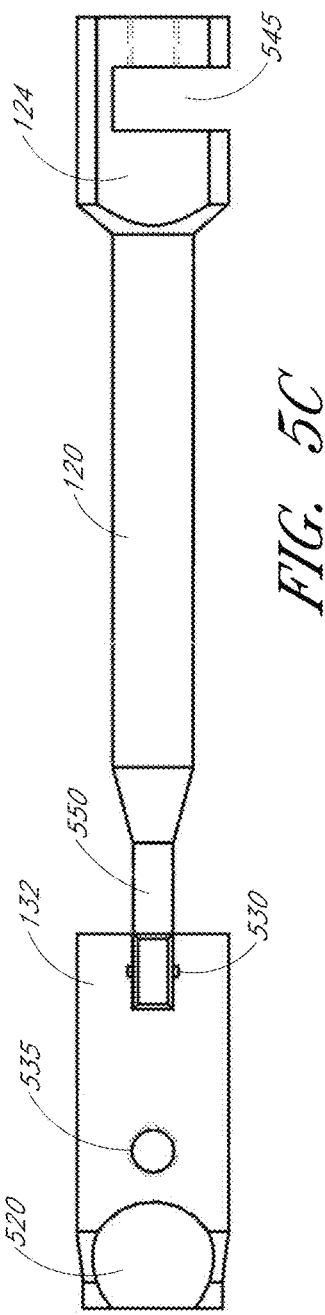
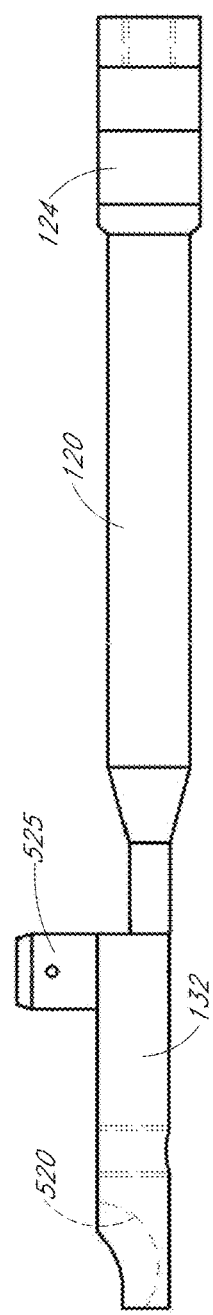
FIG. 5D
FIG. 5C
FIG. 5E

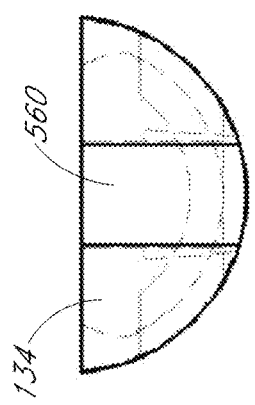
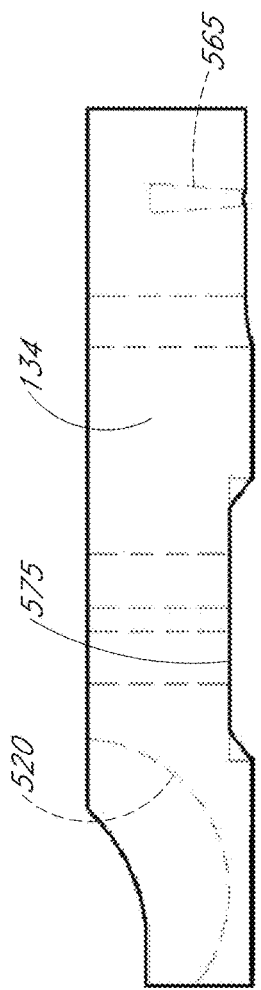
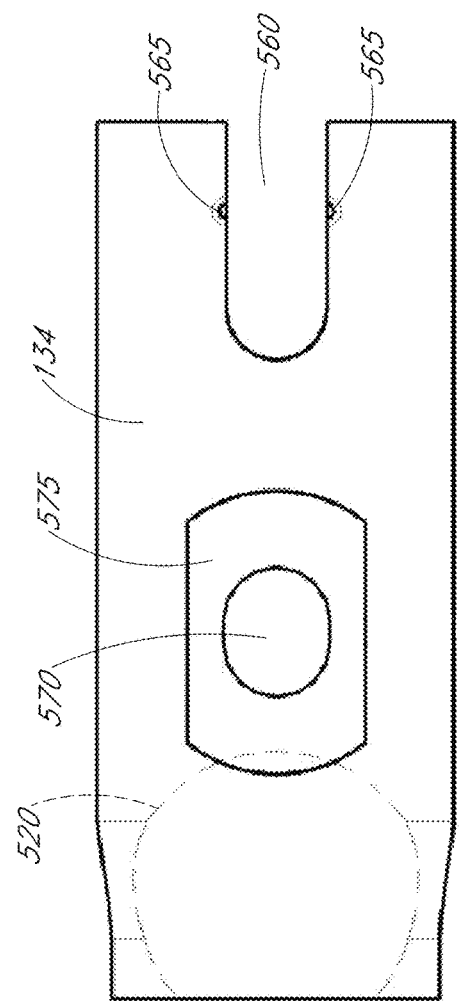

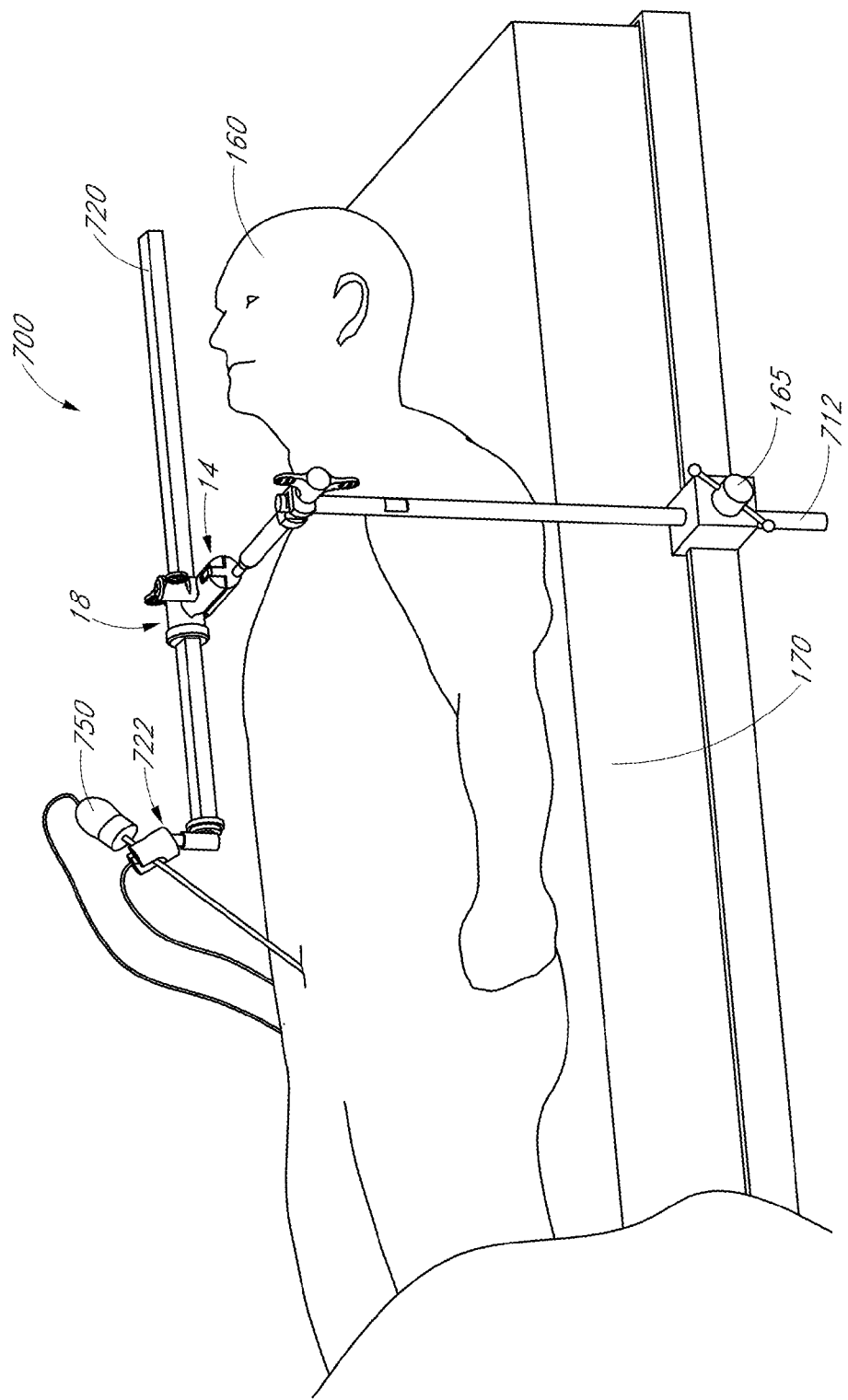

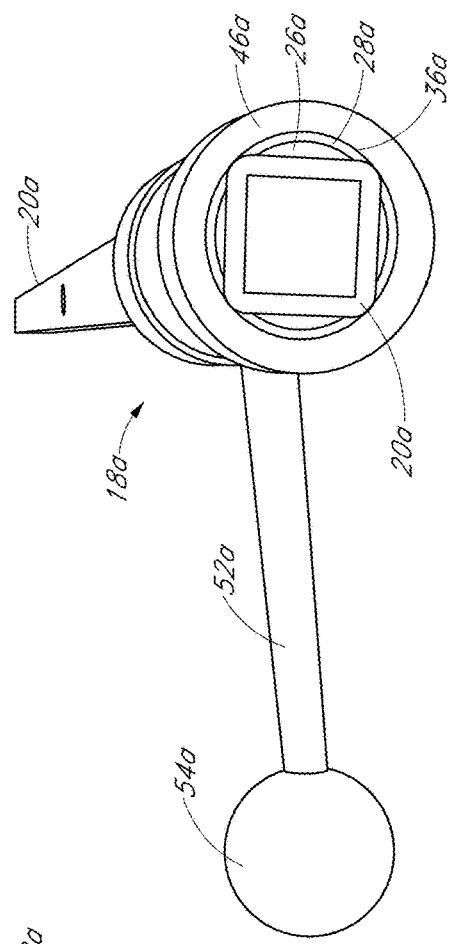
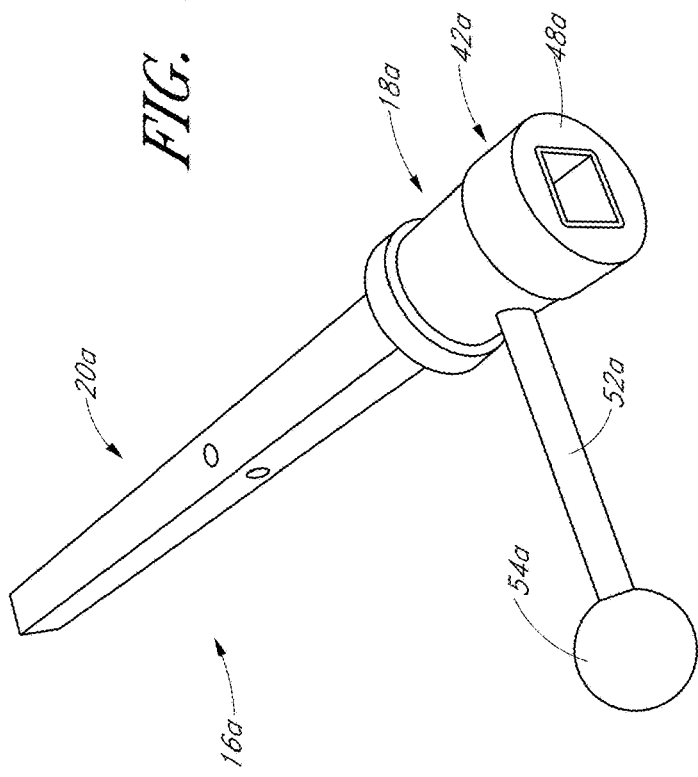

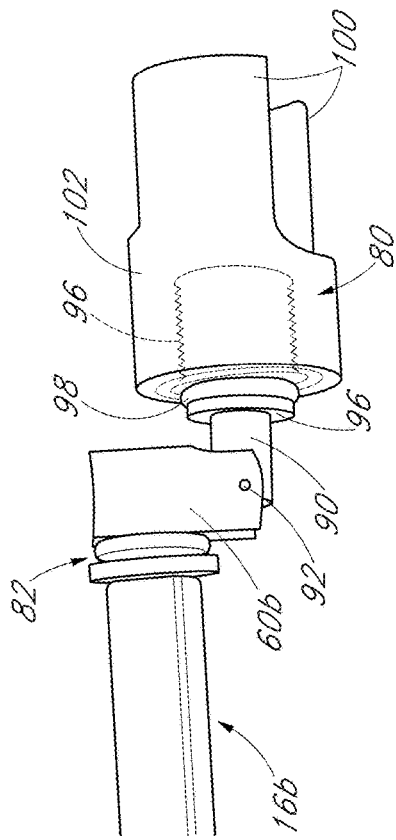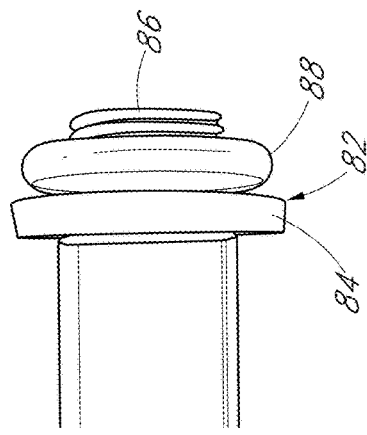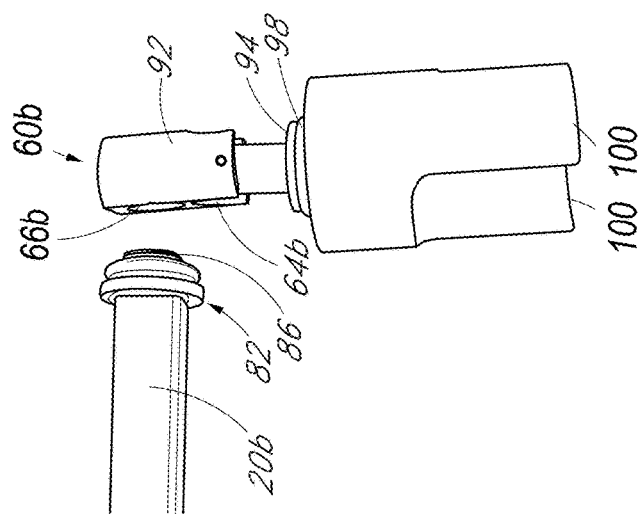

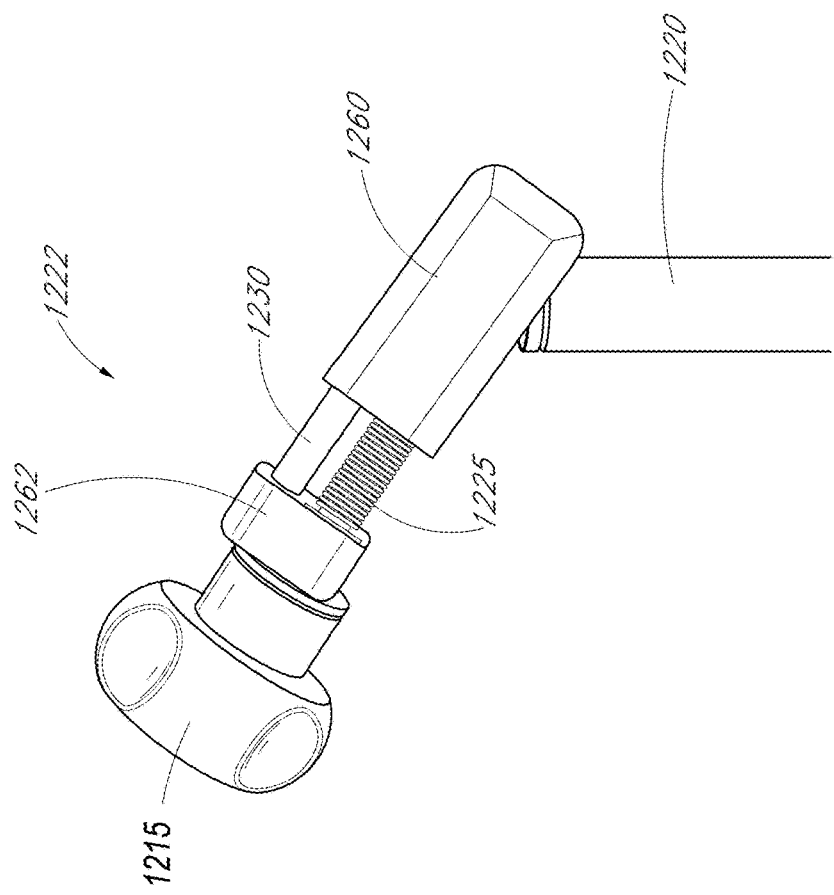
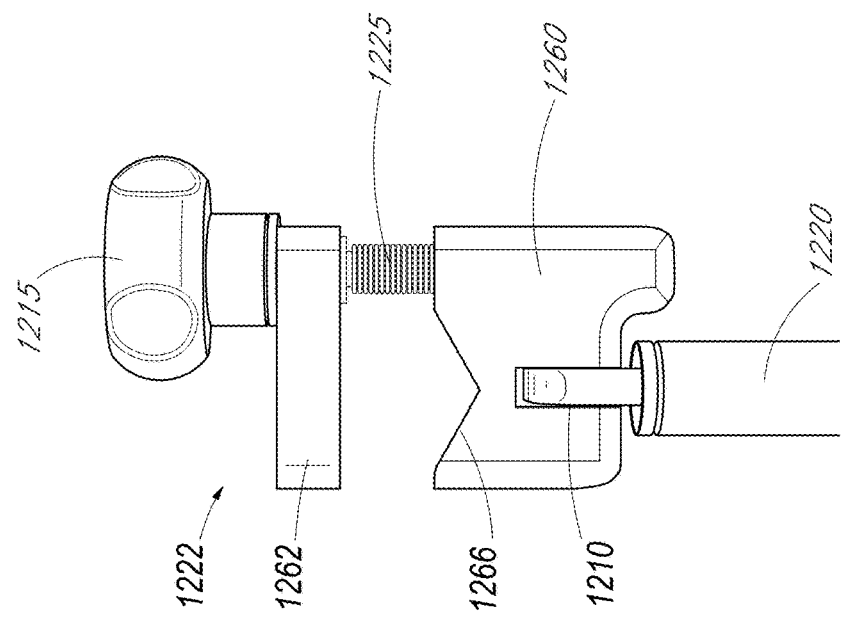
FIG. 12B
FIG. 12A

REPOSITIONABLE MEDICAL INSTRUMENT SUPPORT SYSTEMS, DEVICES, AND METHODS

CROSS-REFERENCE TO RELATED APPLICATIONS

This application is a divisional of U.S. application Ser. No. 14/387,209, filed May 1, 2015, and titled REPOSITIONABLE MEDICAL INSTRUMENT SUPPORT SYSTEMS, DEVICES, AND METHODS, which is a National Stage of PCT Application No. PCT/US2013/037417, filed Apr. 19, 2013, and titled REPOSITIONABLE MEDICAL INSTRUMENT SUPPORT SYSTEMS, DEVICES, AND METHODS, which claims the benefit of U.S. Provisional Application No. 61/636,034, filed Apr. 20, 2012, and titled SUPPORT COUPLING AND ASSOCIATED MEDICAL INSTRUMENT HOLDER. Each of the foregoing applications is hereby incorporated by reference herein in its entirety.

BACKGROUND

Field

The disclosure relates generally to the field of medical instrument supports, and more specifically to repositionable medical instrument support systems, devices, and methods.

Description

Laparoscopic gynecological surgery can be performed as traditional straight stick surgery or robotic surgery. Laparoscopic straight stick surgery usually requires a pelvic assistant to hold a uterine manipulator and manipulate the uterus on command of the surgeon, and an assistant to hold a laparoscopic camera for a surgeon to view the abdominal and pelvic contents. The pelvic assistant sits between the legs of the patient who is in a lithotomy position with a monitor screen placed behind the assistant for the surgeon to see the pelvic contents. The only way the assistant can get a view is to turn his or her head to see the screen, or by providing a slave screen which is placed at a head end of the patient. However, the head end area is often occupied by anesthetics screens and overhead theatre lights, so the pelvic assistant has to resort to head turns for vision.

With the advent of the da Vinci robot in gynecological surgery, the pelvic assistant is still required to sit between the legs of the patient and manipulate the uterine manipulator. However, the assistant is at risk of being hit by an articulated arm of laparoscopic instruments which are controlled by the surgeon. In robotic surgery, there is also an abdominal assistant who has a laparoscopic port to manipulate a laparoscopic instrument such as a sucker or to introduce suture material. The laparoscopic camera is held by one arm of the da Vinci robot.

The pelvic assistant at both the straight stick and robotic surgery is subject to tedious and occupational health and safety issues associated with the operating session. Due to human fatigue and boredom, the pelvic platform that is manipulated for the surgery may not be a stable one, leading to frustration by both parties. Utilizing assistants to hold and/or reposition instruments, such as a uterine manipulator also has other risks. For example, a surgeon must relay instructions to the assistant, which creates a risk that the assistant may not fully understand the instructions and may move the instrument in a way different than the surgeon intended.

SUMMARY

The disclosure herein provides repositionable medical instrument support systems, devices, and methods, including, but not limited to, support couplings and friction-based joint systems. The systems, devices, and methods described herein may be useful to, for example, support a medical instrument in a static position during a medical procedure, while also allowing a user to easily reposition the medical instrument by overcoming a friction force produced at one or more friction-based joints. Any number of medical instruments can be supported with systems, devices, and methods disclosed herein. As non-limiting examples, the instruments could be cameras, sensors, probes, endoscopes including hysteroscopes, curettes, specula, dilators, insufflators, retractors, scissors, ablation tools, forceps, clamps, blades, or ablation elements in some embodiments. In some embodiments, the medical procedure could be an abdominal or vaginal hysterectomy, hysteroscopy, salpingo-oophorectomy, endometrial ablation, sterilization, myomectomy, LEEP conization, laparoscopy, dilation and curettage, or repair of a prolapse for example. In some embodiments, the systems, devices, and methods disclosed herein can be used to support transvaginal, transurethral, transrectal, or transabdominal procedures.

In some embodiments, a support coupling for supporting a support bar comprises a body comprising an axially extending through hole, the hole defining an inner surface of the body, wherein the inner surface comprises at least one seat. The support coupling further comprises at least one resilient member seated in the at least one seat and configured to protrude beyond the inner surface of the hole, the at least one resilient member positioned to be capable of contacting a support bar passing through the hole, wherein the at least one resilient member is configured to create a longitudinal friction force between the support bar and the resilient member along a longitudinal axis of the hole to enable the body to limit translational motion of the support bar along the longitudinal axis until an external force is applied to the support bar that overcomes the longitudinal friction force, and an arm extending from the body to facilitate attachment of the support coupling to a clamp.

In some embodiments of a support coupling, the at least one resilient member is configured to additionally create a rotational friction force between the support bar and the resilient member to enable the body to limit rotational motion of the support bar around the longitudinal axis until an external force is applied to the support bar that overcomes the rotational friction force. In some embodiments, the at least one resilient member comprises an O-ring. In some embodiments, at least one seat is disposed near an end of the hole. In some embodiments, at least one seat comprises an endless or circumferential groove formed on the inner surface about an axis of the hole. In some embodiments, the body comprises a sleeve encapsulating at least a portion of an inner member of the body, wherein the arm is attached to the sleeve. In some embodiments, the arm comprises a ball member positioned at an end of the arm. In some embodiments, at least one opening leading to the hole of the body is non-circular and configured to engage an outer surface of the support bar to resist rotational motion of the support bar around an axis of the hole.

In some embodiments, a repositionable friction-based joint system for providing at least four degrees of freedom comprises an adjustable-friction ball and socket joint configured to provide three degrees of rotational freedom, the ball and socket joint comprising a ball member comprising a substantially spherical structure, a socket comprising at least two clamping members, wherein each of the at least two clamping members comprises a concave surface in contact with the ball member; and an actuator configured to apply a variable actuating force to the at least two clamping members to create a first friction force between the ball member and the clamping members, the first friction force being proportional to the actuating force; wherein the first friction force limits rotational movement of the ball member with respect to the socket until an external force is applied to the ball member to overcome the first friction force. In some embodiments, the joint system further comprises a sliding joint configured to provide one degree of translational freedom, the sliding joint comprising a support coupling comprising a body with an axially extending through hole; a support rod configured to be positioned at least partially within the axially extending through hole; wherein a second friction force between the support coupling and support rod limits translational movement of the support rod through the axially extending through hole until an external force is applied to the support rod to overcome the friction force; and a connecting member attaching the support coupling of the sliding joint to the ball and socket joint.

In some embodiments of a repositionable friction-based joint system, the sliding joint is additionally configured to provide one degree of rotational freedom by allowing the support rod to rotate along a longitudinal axis of the support coupling body. In some embodiments, the second friction force additionally limits rotational movement of the support rod with respect to the support coupling body. In some embodiments, the support coupling of the sliding joint further comprises at least one rotational stop configured to contact an outer surface of the support rod to limit rotational motion of the support rod around a longitudinal axis of the support coupling body. In some embodiments, the second friction force is at least partially created by a resilient member positioned within the axially extending through hole of the support coupling body and in contact with an outer surface of the support rod. In some embodiments, the resilient member comprises an O-ring. In some embodiments, the O-ring is positioned at least partially within a seat of the support coupling body. In some embodiments, the second friction force is adjustable by using a different O-ring. In some embodiments, an outer diameter of the seat is adjustable to adjust the second friction force.

According to some embodiments of a repositionable friction-based joint system, the actuator of the ball and socket joint comprises a threaded member configured to vary the actuating force when turned. In some embodiments, the actuator further comprises a handle configured to enable a human hand to rotate the threaded member. In some embodiments, the actuator comprises a powered actuator. In some embodiments, the powered actuator operates using electrical, pneumatic, or hydraulic power. In some embodiments, the powered actuator is configured to be operated by a remote foot pedal.

According to some embodiments, the connecting member attaches the support coupling of the sliding joint to the ball member of the ball and socket joint. In some embodiments, the connecting member comprises a length configured to position the sliding joint along a centerline of a patient during a medical procedure when the ball and socket joint is in a fixed location relative to a patient support. In some embodiments, the connecting member is replaceable with a connecting member having a different length to enable positioning the sliding joint along a centerline of a patient during a medical procedure when the ball and socket joint is in a fixed location relative to a patient support. In some embodiments, the connecting member comprises a variable length to enable positioning of the sliding joint at variable distances from the ball and socket joint. In some embodiments, the connecting member comprises at least one rod configured to collapse at least partially within a second rod to enable positioning of the sliding joint at variable distances from the ball and socket joint.

In some embodiments, a repositionable medical instrument support system comprises a frame for rigidly connecting the system to a patient support; a ball and socket joint configured to provide three degrees of rotational freedom, the ball and socket joint comprising a ball member at least partially surrounded by a clamping member, wherein the clamping member is adjustable to vary a first friction force between the clamping member and the ball member; a frame mounting arm configured to releasably mount the ball and socket joint to the frame; a sliding joint configured to provide one degree of translational freedom, the sliding joint comprising a support coupling and a support bar passing through the support coupling, wherein a resilient member positioned between the support coupling and support bar creates a second friction force between the support coupling and the support bar; a connecting arm configured to connect the sliding joint to the ball and socket joint; and a docking member configured to engage a medical instrument to support the medical instrument during a medical procedure, the docking member comprising a base portion pivotally coupled to an end of the support bar and having a recess passing there through for receiving a portion of a medical instrument; wherein the first friction force and second friction force can be of a magnitude that enables the support system to support the medical instrument during a medical procedure, but that also enables the medical instrument and support system to be repositioned by applying an external force to the support system that overcomes one or both of the first and second friction forces.

According to some embodiments, the patient support is a table. In some embodiments, the sliding joint is additionally configured to provide one degree of rotational freedom between the support coupling and support bar. In some embodiments, the sliding joint is configured to limit rotational movement of the support rod about an axis of the support coupling by engaging an outer surface of the support rod with a non-circular opening of the support coupling. In some embodiments, the base portion of the docking member is pivotally coupled to the support rod using more than one pivot joint.

Some embodiments further comprise at least one additional ball and socket joint, frame mounting arm, sliding joint, connecting arm, and docking member connected to the frame to enable simultaneous supporting of more than one medical instrument. In some embodiments, the frame comprises at least two mounting locations, wherein the at least two mounting locations are each configured to accept a frame mounting arm and are positioned to allow at least two frame mounting arms to be simultaneously mounted to the frame. In some embodiments, the at least two mounting locations comprise a flat configured to accept a clamp portion of the mounting arm. In some embodiments, the connecting arm has a variable length to allow positioning the sliding joint at various distances from the ball and socket joint. In some embodiments, the connecting arm is replaceable with a connecting arm having a different length to allow positioning the sliding joint at various distances from the ball and socket joint.

According to some embodiments, the first friction force is adjustable by turning a handle connected to a threaded member of the clamping member. In some embodiments, the first friction force is adjustable by actuating an actuator connected to the clamping member. In some embodiments, the docking member further comprises a docking nut engagable with the base portion to clamp the portion of the medical instrument received by the recess of the base portion. In some embodiments, the base portion comprises a screw thread engagable with a screw thread of the docking nut to enable clamping of the portion of the medical instrument received by the recess of the base portion.

In some embodiments, a support coupling comprises a body provided with an axially extending through hole, the hole having an inner surface; and, at least one resilient member seated inside the body and configured to protrude beyond the inner surface of the hole, the at least one resilient member capable of contacting a support bar passing through the hole.

In some embodiments, the support coupling comprises a seat provided in the inner surface of the hole for each of the at least one resilient member, and wherein the or each resilient member is retained in a respective seat. In some embodiments, the or each seat comprises an endless or circumferential groove formed in the inner surface about an axis of the hole. In some embodiments, the or each resilient member comprises a respective O-ring. In some embodiments, a first of the seats is disposed near one end of the hole. In some embodiments, the through hole has first and second openings one at each of respective ends of the body, and wherein the openings are of the same shape. In some embodiments, both openings are circular in shape. In some embodiments, the through hole has first and second openings respective ones of which are at opposite ends of the body, and wherein the first and second openings are of different shape. In some embodiments, the first opening is non-circular and the second opening is circular. In some embodiments, the non-circular shape is selected from the group consisting of: a square, a rectangle, a hexagon, and an ellipse.

In some embodiments, the body comprises a main portion and a demountable first stop attached at one end of the main portion, the stop having an aperture in alignment with the through hole, the aperture forming the first opening of the hole, and wherein the stop extends radially beyond an outer surface of the main portion. In some embodiments, the body comprises a second stop at an opposite end of the main portion, the second stop extending radially beyond the outer surface of the main portion. In some embodiments, the second stop is demountably or removably coupled to the main portion. In some embodiments, the support coupling comprises an integrally formed arm extending from the body to facilitate attachment of the body to a clamp. In an alternate embodiment the support coupling comprises a sleeve locatable about the body and provided with an arm to facilitate attachment of the body via the sleeve to a clamp. In some embodiments, the sleeve is retained on the body by the first stop.

In some embodiments, the support coupling comprises a sleeve locatable about the body and provided with an arm to facilitate attachment of the body via a sleeve to a clamp, the sleeve being retained on the body between the first and second stops. In some embodiments, the arm is provided with a ball structure at a free end.

According to some embodiments, a medical instrument holder configured to support one or more instruments with one or more degrees of freedom of motion comprises a frame connectable to a support; one or more rods; and one or more support couplings, wherein at least one of the rods is coupled to the frame by one of the support couplings wherein the rod passes through the through hole of a corresponding support coupling and is supported in a position by friction between the resilient member and the rod, the rod being movable relative to the support coupling with at least one degree of freedom by application of an external force to overcome the friction.

In some embodiments, the at least one degree of freedom comprises a first degree of freedom being a linear motion in a direction of the rod. In some embodiments, the at least one degree of freedom comprises freedom to rotate about a longitudinal axis of the rod. In some embodiments, the medical instrument holder comprises an instrument docking port attached to the rod, the instrument docking port arranged to clamp onto a medical instrument. In some embodiments, the instrument docking port comprises: a docking element pivotally coupled to the rod, the element having a recess passing there through for receiving a shaft or other portion of a medical instrument; and, a docking nut engagable with the element to clamp the shaft or other portion of the medical instrument to the docking element. In some embodiments, the docking element is provided with a screw thread and the docking nut is engagable with the screw thread, wherein the nut is capable of clamping the shaft or other portion of the medical instrument in the recess by screwing down on the thread.

According to some embodiments, a method of supporting a medical instrument during a medical procedure comprises connecting a frame portion of a medical instrument support system to a patient support, wherein the medical instrument support system comprises a ball and socket joint configured to provide three degrees of rotational freedom and a sliding joint configured to provide one degree of translational freedom; engaging a medical instrument with a docking member of the medical instrument support system; providing a reaction force to the medical instrument from the docking member to oppose motion of the medical instrument, wherein the reaction force is transferred from the patient support through at least the ball and socket joint and sliding joint to the docking member; and positioning the medical instrument by overcoming a friction force of at least one of the ball and socket joint and sliding joint.

In some embodiments of a method of supporting a medical instrument during a medical procedure, a ball and socket joint comprises a ball member at least partially surrounded by a clamping member, wherein the clamping member is adjustable through a continuous range to vary a first friction force between the clamping member and the ball member. In some embodiments of a method of supporting a medical instrument during a medical procedure, a sliding joint comprises a support coupling and a support bar passing through the support coupling, wherein a resilient member positioned between the support coupling and support bar creates a sliding joint friction force between the support coupling and the support bar. In some embodiments of a method of supporting a medical instrument during a medical procedure, a sliding joint is further configured to provide one degree of rotational freedom.

BRIEF DESCRIPTION OF THE DRAWINGS

The foregoing and other features, aspects, and advantages of the present invention are described in detail below with reference to the drawings of various embodiments, which are intended to illustrate and not to limit the invention.

FIG. 2 illustrates a perspective view of an embodiment of a medical instrument support system capable of holding, supporting, and/or repositioning one or more medical instruments.

FIG. 3A illustrates a perspective view of an embodiment of a docking member of a medical instrument support system.

FIG. 3B illustrates a front view of the docking member of FIG. 3A.

FIG. 3C illustrates a front view of an embodiment of a the docking nut of a medical instrument support system.

FIG. 4A illustrates an exploded view of an embodiment of a support coupling of a medical instrument support system.

FIG. 4B illustrates a perspective view of the support coupling of FIG. 4A.

FIG. 4C illustrates a cross-sectional view of a body of the support coupling of FIG. 4A.

FIG. 4D illustrates a cross-sectional view of a first stop of the support coupling of FIG. 4A.

FIG. 5B illustrates a perspective view of various elements of the support system.

FIG. 5C illustrates a top view of an embodiment of a first portion of a clamp assembly of a medical instrument support system.

FIG. 5D illustrates a side view of the first portion of the clamp assembly of FIG. 5C.

FIG. 5E illustrates a front view of the first portion of the clamp assembly of FIG. 5D.

FIG. 5F illustrates a front view of an embodiment of a shell of a clamp assembly of a medical instrument support system.

FIG. 5G illustrates a side view of the shell of FIG. 5F.

FIG. 5H illustrates a top view of the shell of FIG. 5G.

FIG. 7 illustrates an embodiment of a medical instrument support system supporting a medical instrument.

FIG. 9B illustrates a perspective view of an embodiment of a support coupling in use with a support rod of a medical instrument support system.

FIG. 9C illustrates another perspective view of the support coupling and support rod of FIG. 9B.

FIG. 10A illustrates an exploded view of an embodiment of a medical instrument holder of a medical instrument support system.

FIG. 10B illustrates a side view of the medical instrument holder of FIG. 10A.

FIG. 10C illustrates a closer view of a portion of the exploded view of the medical instrument holder of FIG. 10A.

FIG. 12A illustrates a front view of an embodiment of a docking port of a medical instrument support system.

FIG. 12B illustrates a side view of the docking port of FIG. 12A.

DETAILED DESCRIPTION

Figure 1A:
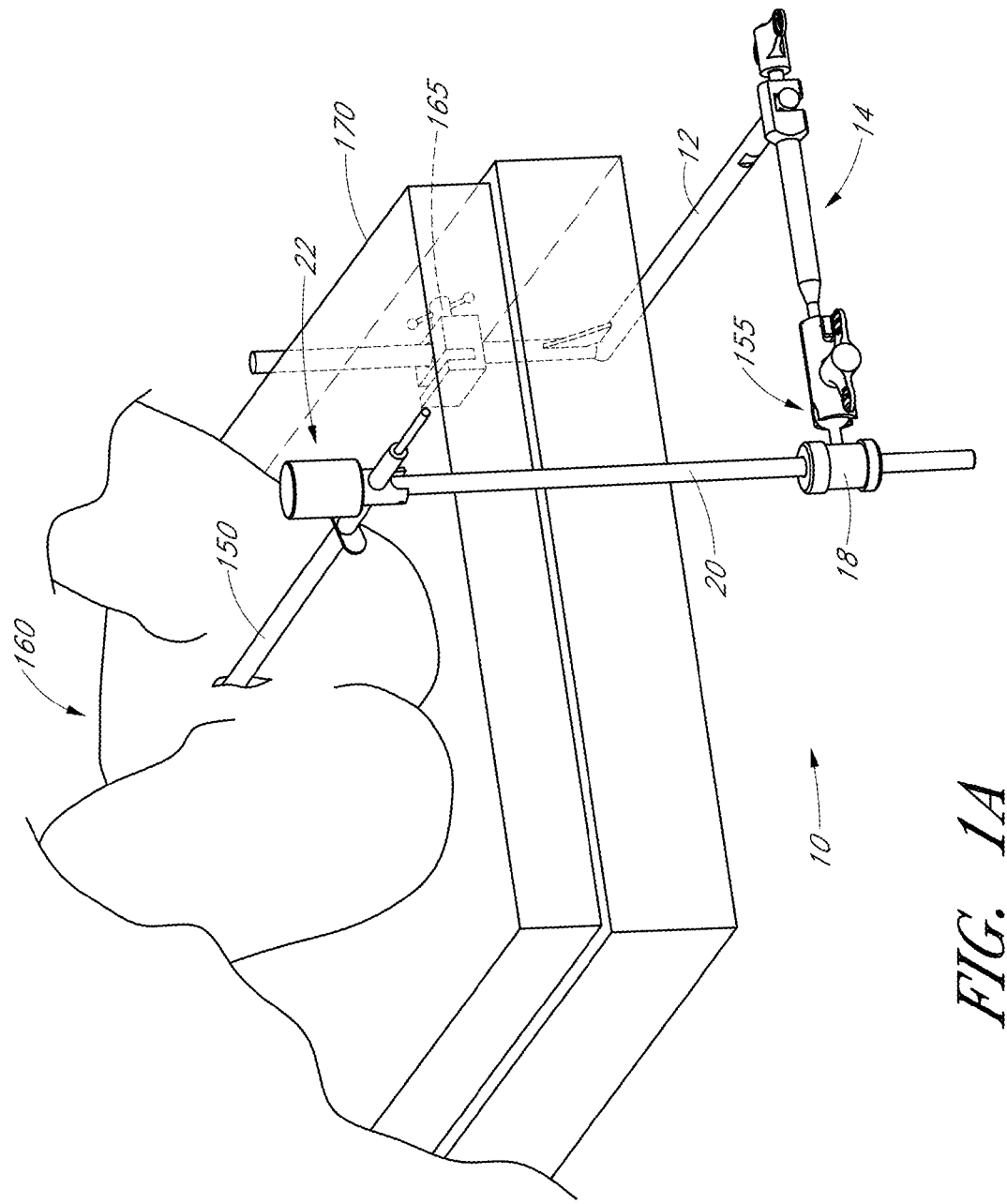
FIG. 1A illustrates a perspective view of an embodiment of a medical instrument support system in use with a patient.

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying FIGS., wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature may be solely responsible for its desirable attributes or is essential to practicing the inventions herein described.

The disclosure herein provides repositionable medical instrument support systems, devices, and methods. In an embodiment, a medical instrument support system simulates a human arm to support a medical instrument during a medical procedure. The medical instrument support system is configured to be repositionable to allow a doctor to reposition the medical instrument on demand as the medical procedure is being performed. For example, a medical instrument support system according to an embodiment of the present disclosure can be configured to support a uterine positioner during a gynecological surgical procedure.

A repositionable medical instrument support system may be desirable, for example, because a doctor may require that a patient's uterus and related organs be repositioned during a gynecological procedure. For example, during a procedure a doctor may require that a patient's uterus be positioned in an up or antiverted position for portions of the procedure but then repositioned in a down or retroverted position during other portions of the procedure. Additionally, while the uterus is in the up or down position, the procedure may require that the uterus be moved from side to side during the procedure. Therefore, it is desirable to have a medical instrument support system that is able to statically maintain a medical instrument in a desired position but to also be easily and quickly repositionable.

During laparoscopic surgery and various other medical procedures, one or more assistants are often required to help support and/or position and/or reposition medical instruments at the direction of the doctor or surgeon. For example, during laparoscopic gynecological surgery, an assistant is often required to sit between the patient's legs to hold a uterine positioner instrument. A surgery can take an extended period of time and lead to fatigue in the assistant holding the positioner. A doctor will often be required to relay instructions to the assistant to instruct the assistant to reposition the patient's uterus by repositioning the uterine positioner. This can introduce risk into a procedure, for example, because the assistant may not fully understand the doctor's instructions. Additionally, the assistant's fatigue may cause the medical instrument to move or drift during the procedure.

One advantage to using an assistant to support and/or reposition a medical instrument is that the human arm incorporates various joints allowing multiple degrees of freedom of motion when positioning the instrument. For example, a human arm has a ball and socket joint at the shoulder providing three degrees of rotational freedom. A human elbow has a pivot joint enabling an additional degree of rotational freedom. A human wrist incorporates a double pivot joint allowing two more degrees of rotational freedom. The bones between a human's wrist and elbow additionally allow a human wrist to rotate about an axis of the forearm, providing for yet another rotational degree of freedom. The various joints of a human arm allow a human hand to be positioned in various ways and in various locations with respect to the person's shoulder and allows the hand to be positioned to accommodate nearly any medical instrument positioning required.

Although the various joints of a human arm provide many benefits in supporting and repositioning medical instruments during medical procedures, utilizing a human assistant introduces several risks to the procedure. For example, the assistant may become fatigued, causing the instrument to drift or be incorrectly positioned. Additionally, the doctor must relay instructions through the assistant rather than adjusting the medical instrument himself or herself. The systems, methods, and devices disclosed herein provide medical instrument supports that simulate or approximate the jointed system of a human arm, but that allow the doctor to easily position and reposition the medical instrument himself or herself. Such a medical instrument support can eliminate the risk of fatigue, because the medical instrument support is holding the medical instrument in place rather than a human arm. The medical instrument support can also eliminate the risks associated with having to provide verbal instructions to an assistant by being directly repositioned by the doctor. Such a medical instrument support can be useful to a doctor in both surgical settings and office settings.

In some embodiments, a medical instrument support system is provided that comprises multiple joints to at least partially simulate the freedom of motion of a human arm and hand. At least some of the joints of the medical instrument support system can be configured to require a certain level of external force be applied to them to overcome a static friction of the joint. The static friction of the joints can be configured to be sufficient to hold the medical instrument support system in a static position, therefore holding the medical instrument in a static position, but still allow a doctor to reposition the support system and medical instrument on demand by overcoming the static friction at one or more of the system's joints. Some medical instrument support systems comprise more joints or degrees of freedom of movement than others. While additional degrees of freedom may allow a medical instrument to be positioned more ways, in some embodiments, having more degrees of freedom than a human arm may in some cases be harder to reposition, because the human brain may not be used to positioning joint systems having that many degrees of freedom.

In some embodiments, a medical instrument support system comprises a ball and socket joint to simulate a human shoulder joint. In some embodiments, the ball and socket joint is an adjustable-friction joint. For example, the ball and socket joint may be configured to allow a user to adjust the pressure or force within a predetermined range that the socket portion applies to the ball portion. This adjustability in the friction of the ball and socket joint can be advantageous to, for example, enable the support of medical instruments of varying weights and/or to match the preference of the doctor or user utilizing the medical support system.

In some embodiments, the ball and socket joint is coupled to a support coupling. The support coupling can be configured to engage a support rod and to allow the support rod to be repositioned along a central axis of the support coupling, providing one degree of translational motion. In some embodiments, the support coupling is also configured to allow a degree of rotational motion, allowing the support rod to rotate about the same central axis of the support coupling. In some embodiments, the support coupling incorporates at least one resilient member to apply a friction force to the support rod passing through the support coupling. The resilient member can be, for example, an O-ring. Depending on various parameters, such as a thickness of the resilient member and friction coefficients of the various components, a variable amount of friction can be generated between the support coupling and the support rod. The friction between the support coupling and support rod can be optimized to enable the support rod to remain statically positioned when supporting a medical instrument during a medical procedure, but to allow a doctor or other user to reposition the medical instrument by overcoming the friction between the support coupling and support rod by applying an external force to the support rod.

In some embodiments, a medical instrument support system additionally comprises one, two, or more docking ports attached to the support rod and configured to engage one, two, or more medical instruments. In some embodiments, the docking port is connected to the support rod through one or more pivot joints in order to simulate a human wrist joint. The one or more pivot joints may be used to simulate a human wrist pivoting with respect to the forearm. The docking port may also be configured to rotate with respect to the support coupling by rotating the support rod within the support coupling in order to simulate the rotation of a human wrist with respect to the elbow joint.

When a human assistant is supporting a medical instrument during a medical procedure, the assistant's muscles must maintain tension on the assistant's various arm joints to maintain the medical instrument in a static position. In various embodiments described herein, medical instrument support systems incorporate joints with a certain amount of friction intended to simulate or approximate the tension a human assistant's muscles must maintain. For example, the friction in an adjustable-friction ball and socket joint simulates the tension an assistant's muscles must keep on the assistant's shoulder joint in supporting a medical instrument. The joint or joints at the docking port may also incorporate a certain level of friction intended to simulate the tension required to keep a user's wrist from pivoting. The resilient member within the support coupling can, for example, simulate the tension in an arm required to resist the wrist from rotating with respect to the elbow. The resilient member can also simulate the tension required in various arm muscles to keep the human wrist from translating with respect to the shoulder.

In various embodiments, repositionable medical instrument support systems are provided that require no power to maintain their position. This can be advantageous, for example, to reduce complexity and/or cost of the support system and to eliminate a potential failure point were power to be lost. As an example of the reduction in complexity, a powered medical instrument support system would likely require a switch to engage or disengage the support system, such as a remote foot pedal. This would require that a doctor perform an additional step in repositioning the medical instrument support system. However, in various embodiments disclosed herein, the medical instrument support system can be directly repositioned by merely grabbing a portion of the medical instrument support system with the user's hand and repositioning it directly, without having to disengage any locking features or similar devices.

One option in creating a medical instrument support system is to utilize joints having a locked or unlocked configuration. For example, a medical instrument support system may have joints that allow the supporting of a medical instrument when all joints are locked but that requires the joints be unlocked to reposition the instrument. In these systems, a risk is introduced that, when one or more joints is unlocked, the medical instrument may fall or reposition itself to a position that is not desired. Additionally, the person repositioning the support system may have to hold the system using both hands while repositioning it with the joints unlocked. Further, a patient may sometimes move or slip during a medical procedure. Particularly, when a patient is put in a Trendelenburg position (i.e. head down), the patient's body has been known to sometimes slip. If a medical instrument is supported by a "locked" system when the patient moves, the medical instrument may injure the patient, such as by puncturing an organ and/or placing an unexpected force on the patient's body. In various embodiments described herein, however, medical instrument support systems are provided that include joints with a certain level of friction that can be overcome when repositioning the system (or when the patient slips or moves) rather than requiring one or more joints to be unlocked to be repositioned. However, in some embodiments one or more joints can be provided having binary locked or unlocked configurations. In some embodiments, a medical instrument support system can be repositioned by a doctor using a motion similar to shifting a gear shifter in a car. For example, the doctor can grab the docking port portion of the system and simply push, pull, or rotate the docking port to whatever position the doctor desires it be in.

Another option in creating a medical instrument support system is to utilize powered joints that are actuated using, for example, motors or powered actuators. In such a medical instrument support system, motors or powered actuators are used to move the joints and to reposition the medical instrument. However, a substantial risk with such a system is that a human's organs can be perforated, leading to injury and/or death, when the system incorrectly positions a medical instrument, such as from a computer programming malfunction or operator error. For example, a powered system may accidentally insert a medical instrument too far into a patient. An advantage of a human-powered system, such as the medical instrument support systems described herein, is that the system remains under human control, and is not vulnerable to computer programming malfunctions or the risks associated with a human operating remote controls.

Although various embodiments described herein are described in reference to medical procedures such as surgical procedures, various embodiments of medical instrument holders described herein may also be useful in nonsurgical procedures, such as gynecological or other office procedures. The systems, devices, and methods described herein may be advantageous in an office setting in addition to a surgical setting for many of the same reasons such a system, device, or method may be advantageous in the surgical setting. For example, a support system may eliminate the issue of user fatigue. A system may also eliminate the need for an assistant to be positioned in a position holding a medical instrument, therefore freeing up space for the doctor to maneuver. A system as described herein may additionally be advantageous to reduce operating costs of a medical office. A doctor may be able to utilize a support system as described herein instead of requiring one or more assistants to support medical instruments. Various systems, methods, and devices described herein may additionally be useful in fields other than the medical field. For example, a support system may be useful any time one requires that an object be held in a certain position and easily repositioned to other positions.

In various embodiments, medical instrument support systems are configured to allow disassembly and/or are configured to be compactible to fit into an autoclave for sterilization. In some embodiments, every component of a medical instrument support system consists of materials capable of withstanding an autoclave process and being reused in various medical procedures.

FIG. 1A illustrates a perspective view of an embodiment of a medical instrument support system 10 in use with medical instrument 150 and a patient 160. As shown in FIG. 1A, the patient 160 is positioned on a patient support or table 170. The medical instrument support system 10 is affixed to the patient support table 170 at one end using a support clamp 165 and is supporting a medical instrument 150 at another end. In this embodiment, the medical instrument 150 is a uterine manipulator inserted through a vagina of the patient 160 to engage the patient's uterus and enable positioning of the patient's uterus during a medical procedure.

The medical instrument support system 10 comprises a frame 12, a clamp assembly 14, a support coupling 18, a support rod 20, and a docking port or docking member 22. The frame 12 is rigidly attached to the patient support table 170 at an end of the frame 12. The clamp assembly 14 is attached to the frame 12 at another end of the frame 12. The clamp assembly 14 utilizes a releasable clamp at one end of the clamp assembly 14 to releasably attach the clamp assembly 14 to the frame 12. An adjustable-friction ball and socket joint 155 is positioned at an opposite end of the clamp assembly 14 and connected to the support coupling 18. The ball and socket joint 155 is configured to allow the support coupling 18 to move with three degrees of rotational freedom with respect to the clamp assembly 14. The support rod 20 is positioned to slide within a lumen, hole, or aperture of the support coupling 18 creating a sliding joint allowing for one degree of translational freedom between the support coupling 18 and the support rod 20. In this embodiment, the support rod 20 is generally cylindrical in shape and also has one degree of rotational freedom with respect to the support coupling 18 about a central axis of the support coupling 18. The docking port 22 is positioned at or near a free end of the support rod 20 and configured to clamp onto the medical instrument 150 to enable supporting and/or positioning of the medical instrument 150. In some embodiments, the docking port 22 is configured to hold medical instruments having an outer diameter of up to 5 or 7 or more centimeters.

In some embodiments, the support rod has a length of up to one meter. A support rod having a length of up to one meter may be advantageous for use in, for example, supporting gynecological instruments. In some embodiments, the support rod has a length of up to five meters or more. A support rod having a length of up to five meters or more may be advantageous for use in, for example, supporting human limbs or distant instruments. In embodiments having relatively long support rods, it may be advantageous to utilize more robust ball and socket joints, support couplings, powered actuators (such as the powered actuator illustrated in FIG. 13), and/or other components of the system.

Figure 1C:
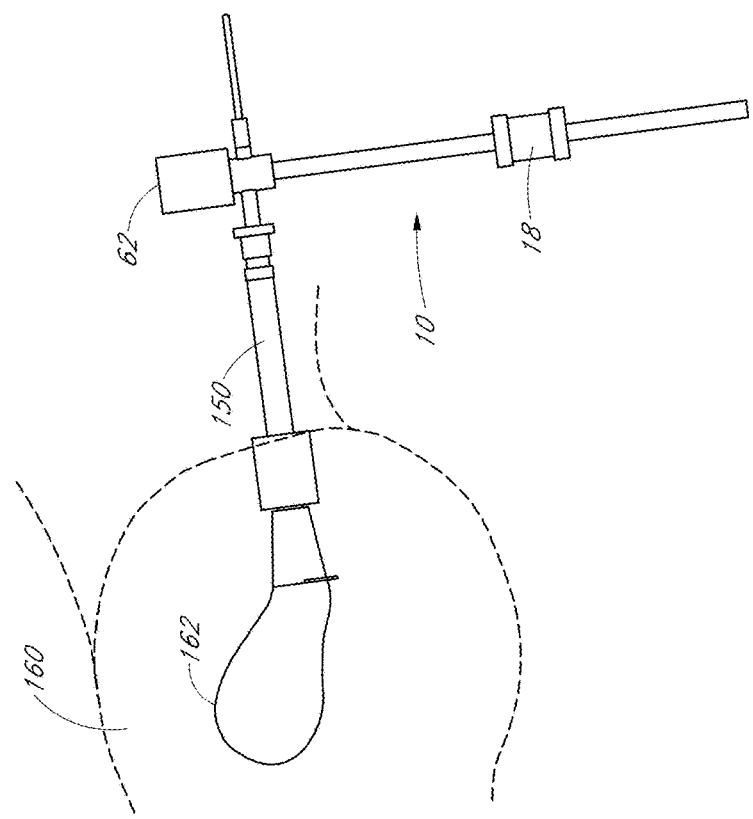
FIG. 1C illustrates a side view of an embodiment of a medical instrument support system positioning a medical instrument and therefore a patient's uterus in a down or retroverted position.
Figure 1B:
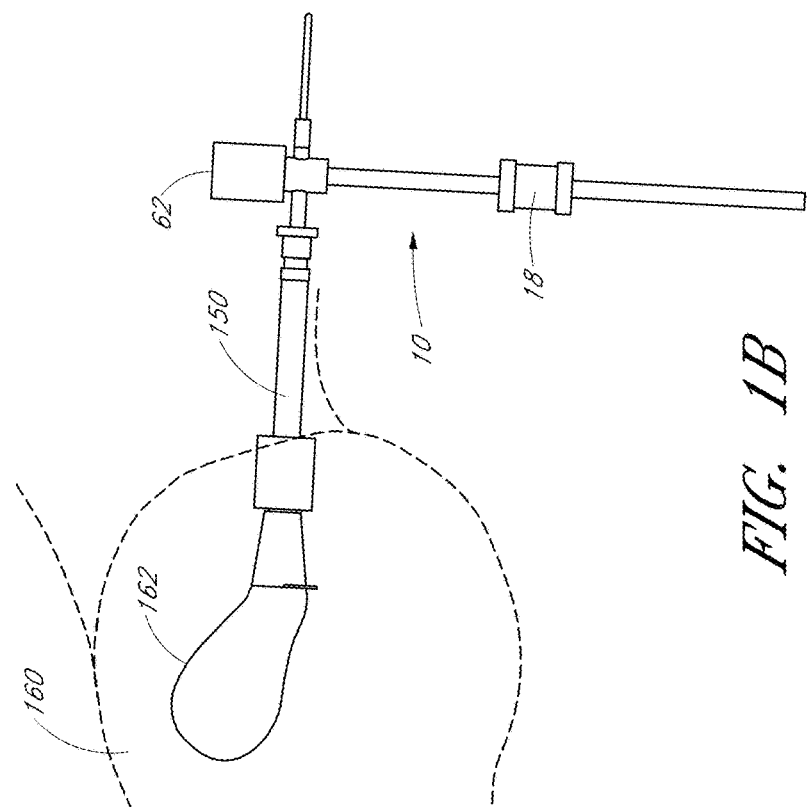
FIG. 1B illustrates a side view of an embodiment of a medical instrument support system positioning a medical instrument and therefore a patient's uterus in an up or antiverted position.

The medical instrument support system 10 illustrated in FIG. 1A enables the support of the medical instrument 150 and also the easy repositioning of the medical instrument 150. As an example, FIGS. 1B and 1C illustrate side views of a portion of the medical instrument support system 10 with the medical instrument 150 in two different positions. FIG. 1B illustrates the medical instrument support system 10 positioning the medical instrument 150 and therefore the patient's uterus 162 in an up or antiverted position. FIG. 1C, on the other hand, illustrates the medical instrument support system 10 positioning the medical instrument 150 and therefore the patient's uterus 162 in a down or retroverted position. The docking nut 62 of the docking port 22 can be utilized as a handle for a doctor to reposition the medical instrument support system 10. In some embodiments, the medical instrument support system 10 is configured to allow the docking port 22 to move within 0.5 meter radius of movement.

In use, the medical instrument support system 10 is configured to support a medical instrument 150 by providing reactive forces to keep the medical instrument 150 in a static position. For example, in the configuration shown in FIGS. 1A, 1B, and 1C the medical instrument 150 is cantilevered out of the patient's vagina. To maintain the medical instrument 150 in a static position, the medical instrument support system 100 must therefore provide a reaction force to counteract a downward force of gravity acting on the cantilevered portion of the medical instrument 150. In this embodiment, the downward force from the medical instrument 150 acts through the docking port 22 into the support rod 20, into the support coupling 18, where the load is transferred to the clamp assembly 14, to be transferred to the frame 12, where the load is finally transferred to the patient support 170. Although the primary force required to be counteracted by the medical instrument support system 10 in this configuration is a gravity force of the cantilevered portion of the medical instrument 150, the friction of the various joints of the medical instrument support system 10 also allow countering various other forces. For example, if the patient's uterus 162 is positioned to the left or to the right, the medical instrument support system 10 will likely be required to resist a sideways force from the medical instrument 150 tending to try to bring the medical instrument 150 back along a centerline of the patient 160.

FIG. 2 illustrates a perspective view of an embodiment of a medical instrument support system ("MISS") 10 capable of holding, supporting, and/or repositioning one or more medical instruments. The MISS 10 comprises a number of components including a frame 12, a clamp assembly 14, and a medical instrument holder 16. The medical instrument holder 16 comprises a support coupling 18, a support rod 20, and a medical instrument docking port 22. In use, the frame 12 is typically coupled to a support structure such as an operating table by of one or more clamps (not shown). The clamp assembly 14 couples the medical instrument holder 16 to the frame 12. A medical instrument such as, but not limited to, an intra-uterine cannula can be attached to the medical instrument holder 16 via the medical instrument docking port 22.

The support coupling 18 is configured to enable the rod 20 to be moved with one or more degrees of freedom. A first degree of freedom is freedom to move lineally through the support coupling 18 in either direction along the length of the support rod 20. A second degree of freedom is the freedom to rotate in either sense about the axis of the rod 20. However, as explained in greater detail below, the support coupling 18 is arranged to apply a friction force to the rod 20 to prevent motion in the absence of application of a sufficient external force. The friction force enables the rod 20 to substantially maintain its position in the absence of an externally applied over powering force. This over powering force may, for example, be applied by a doctor or pelvic assistant during a surgical procedure. The over powering force may be applied to the docking port 22 or various other locations of the MISS 10.

FIGS. 3A-3C, 4A-4D, 5, and 6A-6B illustrate in greater detail embodiments of some of the components of the MISS 10 illustrated in FIG. 2. FIGS. 3A-3C illustrate embodiments of components of the docking port 22. The medical instrument docking port 22 comprises a docking member 60 and a docking nut 62. FIG. 3A illustrates a perspective view of the docking member 60. FIG. 3B illustrates a front view of the docking member 60. The docking member 60 is configured to be pivotally coupled at one end of the rod 20. Although in this embodiment the docking member 60 is configured to be pivotally coupled to the rod 20 using a single pivot joint, in various other embodiments, the docking member 60 may be coupled to the rod 20 using more than one pivot joint, a ball and socket joint, a combination of pivot joints and ball and socket joints, or any combination of joints allowing relative motion between the docking member 60 and rod 20.

The docking member 60 comprises a general form of a squat solid cylinder having a U-shape channel 64 at one end and a transversely extending circular through hole 66 located between the U-shape channel 64 and an opposite end 68 of the cylinder. A further hole 70 is formed through a portion of the docking member 60 containing the U-shape channel 64. The hole 70 is configured to receive a pivot pin 310 (shown in FIG. 2) which also passes through the rod 20 and pivotally couples the docking member 60 to the rod 20. A screw thread 72 is formed about the docking member 60 extending from the end 68 to a location within the circumferential bounds of the hole 66.

FIG. 3C illustrates a front view of the docking nut 62. The docking nut 62, in some embodiments, comprises a general form of a solid cylinder of material provided with an axially extending blind hole 74 formed with an internal thread 76. The hole 74 is of a depth such that the nut 62 can be screwed onto the docking member 60 for substantially the whole axial length of the thread 72. In use, the docking nut 62 can be threaded onto the docking member 60 and used to clamp a medical instrument in position passing through the hole 66 of the docking member 60.

In various embodiments, the docking member 60 and docking nut 62 (in addition to various other components of a medical instrument support system) can comprise various materials. For example, the components can comprise steel, stainless steel, aluminum, plastic, medical grade materials, or any other material sufficient to perform the functions described herein. In some embodiments, the components comprise materials capable of being sterilized in an autoclave.

FIGS. 4A-4D illustrate in greater detail the structure and configuration of an embodiment of the support coupling 18. FIG. 4A illustrates an exploded view of the support coupling 18. FIG. 4B illustrates a perspective view of the support coupling 18. FIG. 4C illustrates a cross-sectional view of a body 24 of the support coupling 18. FIG. 4D illustrates a cross-sectional view of a first stop 42 of the support coupling 18. This embodiment of a support coupling 18 comprises a body 24 provided with an axially extending through hole, lumen, or aperture 26 and a resilient member 28 seated inside of the body 24. The hole, lumen, or aperture 26 has an inner surface 30 in which the resilient member 28 is seated. The resilient member 28 is configured to protrude beyond the surface 30 so that it is capable of contacting the outer surface of the rod 20 when the rod 20 passes through the hole 26.

The body or inner member 24 is formed with a seat 32 in the surface 30 for seating the resilient member 28. In this embodiment the resilient member 28 is in the form of an O-ring and thus the seat 32 is in the form of a continuous longitudinal groove. The O-ring 28 and seat 32 are configured so that a portion of the O-ring 28 extends from the seat 32 beyond the end surface 30. The degree of extension and/or the amount of friction generated between the O-ring 28 and rod 20 can be varied, for example, by use of O-rings of different sizes within the seat 32. The degree of extension and/or the amount of friction can also be varied by changing parameters of the seat 32, such as increasing an outer diameter of the seat 32, and/or by using O-rings of different compositions having different friction coefficients. Although several embodiments are described herein as utilizing one or more O-rings, various embodiments of support couplings may utilize various other methods of generating friction between the body 24 and the rod 20. For example, the support coupling may comprise a spring-loaded surface forced into contact with an outer surface of the rod 20 by spring pressure, or an expandable member, such as an inflatable member configured to expand in a radially inward direction.

In some embodiments, the support coupling 18 is configured to statically hold at least a predetermined amount of force transferred from the rod 20, but to allow movement of the rod 20 when an external force exceeds that predetermined force. In some embodiments, a support coupling 18 is configured to support a load of approximately 800 grams. In some embodiments, a support coupling 18 is configured to allow the rod 20 to translate with respect to the support coupling 18 when a load of approximately 2 kilograms or 2.5 kilograms is applied. In some embodiments, the force required to move the rod 20 with respect to the support coupling 18 is different to move the rod 20 up than to move the rod 20 down. In the gynecological field, a uterine manipulator typically weighs 800 to 1000 kilograms, and a system requiring approximately 2 or 2.5 kilograms to move the rod 20 can be advantageous. This range can, for example, be sufficient to support the medical instrument during the medical procedure and resist moving as a result of a small, possibly unintentional contact by the user of the system, but also low enough to allow easy repositioning and/or to allow the medical instrument to move if the patient's body slips or otherwise moves during the procedure. In some embodiments, the support coupling 18 is configured to support a larger load by requiring more force to move the rod 20 (such as by using a thicker O-ring 28). In some embodiments, a powered system or mechanical lever is provided to assist in moving the rod 20 with respect to the support coupling 18. This may be advantageous, for example, in situations where the force required to move the rod 20 is relatively high. This may also be advantageous to use with robotic surgery, so the rod 20 can be moved without requiring a human to move the rod 20 directly.

The hole, lumen, or aperture 26, in this embodiment, has circular openings 34 and 36 respectively at opposite ends of the body 24. In the present illustrated embodiment the hole 26 is a circular hole and each of the first and second ends 34 and 36 are the same shape, namely in the shape of a circle. When the rod 20 is similarly of a circular shape, the support coupling 18 provides the two degrees of freedom namely linear sliding motion and a rotation. In various other embodiments, the hole 26 can be non-circular, and/or one or both of the openings 34 and 36 can be non-circular. This may be advantageous to, for example, limit rotational motion of the rod 20 with respect to the support coupling 18 when the rod 20 comprises a non-circular shape.

The support coupling 18 further comprises a main body 40 and a demountable first stop 42. The first stop 42 extends radially from an outer surface of the cylindrical tube 43. The main body 40 is in the form of a cylindrical tube 43 with a screw thread 44 formed at one end, and an integral second stop 46 formed at the opposite end. The second stop 46 also extends radially from an outer surface of the cylindrical tube 43.

The first stop 42 is in the form of a cap which screws onto the screw thread 44 and is formed with an aperture 48. The aperture 48 forms and constitutes the first opening 34 of the through hole 26. Although in this embodiment the first stop 42 is removable, and the second stop 46 is integral to the main body 40, in other embodiments, both stops may be removable or both stops may be permanently attached to the main body 40.

In use, the first stop 42 and/or second stop 46 can be configured to define limits to the translational motion of the rod 20 with respect to the support coupling 18. For example, the stops can be configured to contact a component protruding beyond the outer surface of the rod 20 to stop the support coupling 18 from moving beyond that protruding component.

Figure 5A:
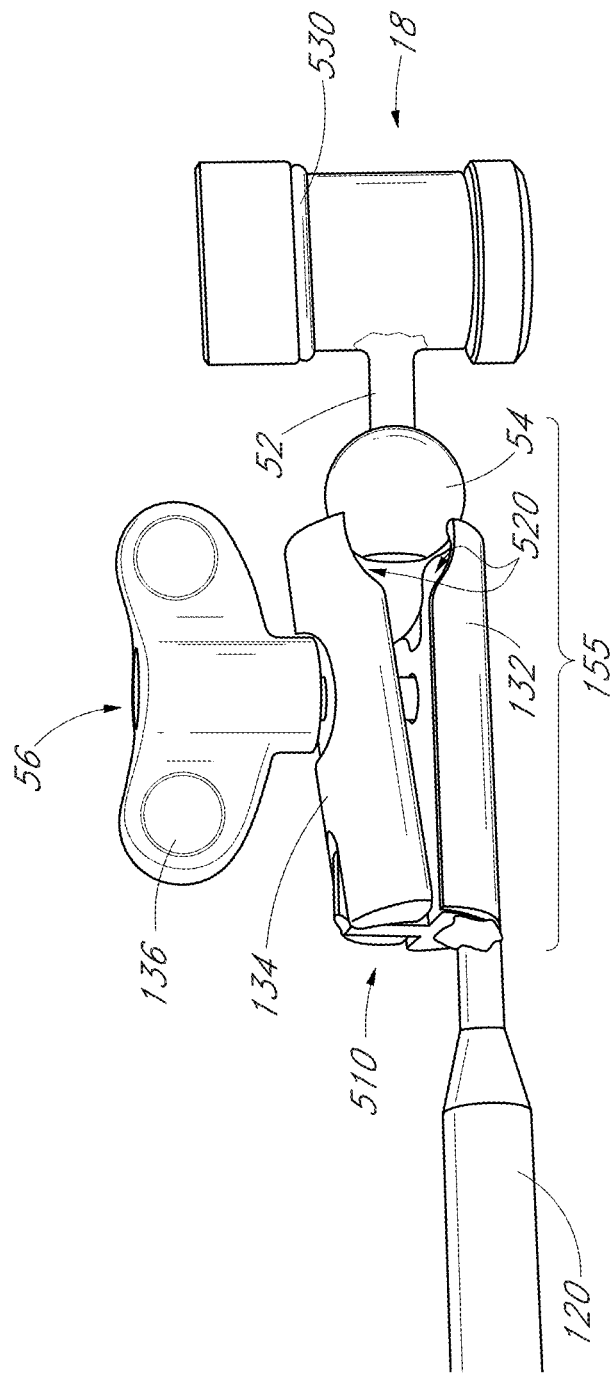
FIG. 5A illustrates an exploded view of an embodiment of a ball and socket joint of a medical instrument support system.

A sleeve 50 encapsulates at least a portion of the body or inner member 24 and is retained on the body 24 by the first stop 42, and more particularly between the first and second stops 42 and 46. In some embodiments, as shown in FIG. 5A, an O-ring is positioned between the first stop 42 and the sleeve 50. In some embodiments, sleeve 50 is retained on the body 24 in a manner so that in normal use there is no rotation between the body 24 and the sleeve 50. This can be achieved by screwing the first stop 42 down sufficiently to clamp the sleeve 50 between the stops 42 and 46. However, this may be augmented, for example, by the provision of one or more longitudinally grooves on the cylindrical tube 43 or the inside of the sleeve 50, and corresponding splines on the other of the cylindrical tube 43 and the sleeve 50.

In some embodiments, the sleeve 50 is retained on the body 24 in a manner so that in normal use rotation is allowed between the sleeve 50 and the body 24. A friction force resisting this rotation may be generated between the sleeve 50 and the end stops and/or an O-ring positioned between an end of the sleeve 50 and a stop. This configuration may be advantageous to, for example, allow independent adjustment of the force required to lineally translate the rod 20 versus the force required to rotate the rod 20.

In some embodiments, an arm or connecting member 52 is integrally formed with and extends transversely from the sleeve 50. A mounting ball or ball member 54 is fixed at the free end of the arm 52. The ball 54 is configured to be received in a ball clamp 56 of the clamp assembly 14, as described below and shown in FIG. 5A. In some embodiments, a length of the arm 52 is configured to allow the support coupling 18 to be positioned along a centerline of the patient when used to support a medical instrument (as shown in FIG. 1A). To enable usage of the medical instrument support system 10 with patient support tables of various dimensions, the length of the arm 52 may be varied to enable positioning the support coupling 18 at various distances from the ball clamp 56. In some embodiments, the entire support coupling 18 is replaced with a support coupling having an arm 52 with a different length. In some embodiments, the sleeve 50 is replaced with a sleeve having an arm 52 with a different length. In some embodiments, the arm 52 is removably coupled to the sleeve 50, allowing the arm 52 to be removed from the sleeve 50 and replaced with an arm of a different length. In some embodiments, the arm 52 is configured be a variable length arm. For example, the arm can comprise two or more sections configured to collapse within each other to make the arm shorter or to telescope to make the arm longer.

In the embodiment shown in FIG. 2, the clamp assembly 14 comprises a rigid bar 120 having a frame clamp 122 fixed at one end and the ball clamp 56 fixed at an opposite end. The frame clamp 122 comprises a C-shaped body 124 with a wing screw 126 threadingly engaged through one end of the body 124. A threaded shaft 128 of the wing screw 126 extends into an opening of the C-shaped body 124 so as to clamp onto a flat land 120 formed in the L-frame 12.

The ball clamp 56 comprises a pair of pivotally coupled shells or clamping members 132 and 134, and a wing screw or actuator 136 which can be tightened and loosened to vary the distance between the shells 132 and 134 and/or to apply a variable actuating force to the shells 132 and 134. In some embodiments, the variable actuating force can be up to 30 kilograms or more. The shell 132 is fixed to the bar 120 and the shell 134 is pivotally coupled at one end to the shell 132. The wing screw 136 engages both shells 132 and 134 at a location intermediate their length. The distant end of the shells 132 and 134 together form a socket for receiving the ball 54. By tightening and loosening the wing screw 136, the compression on the ball 54 can be varied to vary the force required to adjust the orientation of the medical instrument holder 16 relative to the clamps 14 and frame 12. In some embodiments, the force required to adjust the orientation of the medical instrument holder 16 is proportional to the actuating force of the wing screw or actuator 136.

FIG. 5A further illustrates the ball and socket joint 155 formed by the ball clamp 56 and ball 54 of the support coupling 18. FIG. 5A illustrates an exploded view of the ball and socket joint 155. Shown in FIG. 5A is one end of the clamp assembly 14 having a rigid bar 120 and a ball clamp 56. Also shown in FIG. 5A is the support coupling 18. The ball 54 of the support coupling 18 and the ball clamp 56 of the clamp assembly 14 together form the ball and socket joint 155. The ball clamp 56 is affixed to an end of the rigid bar 120. The ball clamp 56 comprises a bottom shell 132, a top shell 134, and a wing screw 136. The top shell 134 is pivotally coupled to the bottom shell 132 at an end using a pivot joint 510. The top shell 134 and bottom shell 132 each comprise a concave surface 520. The concave surfaces 520 are configured to generally conform to a shape of the ball 54. The wing screw 136 comprises a handle and a shaft, the shaft passing through a hole in the top shell 134 and into a hole of the bottom shell 132. A threaded joint causes the wing screw 136 to move up or down with respect to the bottom shell 132 when the wing screw 136 is rotated. For example, when the wing screw 136 is rotated clockwise, the top shell 134 is moved so that its concave surface 520 is closer to the concave surface 520 of the bottom shell 132. When the wing screw 136 is rotated in a counterclockwise direction, the top shell 134 can pivot away from the bottom shell 132.

In use, the generally or substantially spherical ball 54 of the support coupling 18 is inserted into a cavity or socket of the ball clamp 56 formed by the two concave surfaces 520. The wing screw 136 is then rotated in a clockwise direction to bring the two concave surfaces 520 into contact with an outer surface of the ball 54. Because the ball 54 is generally spherical in shape, the support coupling can rotate with respect to the ball clamp 56 in three degrees of rotational freedom. However, the rotation of the support coupling 18 can be restricted by a friction force between the ball 54 and the concave surfaces 520. The magnitude of this friction force can be varied by rotating the wing screw 136 to apply a varying amount of pressure between the concave surfaces 520 and the ball 54. When using the medical instrument support system 10 during a medical procedure, a user can adjust the friction of the ball and socket joint 155 to his or her liking. A user will typically adjust the friction of the ball and socket joint 155 to enable a medical instrument to be held statically, but to also enable easy repositioning of the support coupling 18 with respect to the ball clamp 56 when the user wishes to reposition the medical instrument support system 10. Unlike a system utilizing a locking joint, the user does not have to adjust or unlock the ball and socket joint 155 in order to reposition the medical instrument support system 10.

Figure 5J:
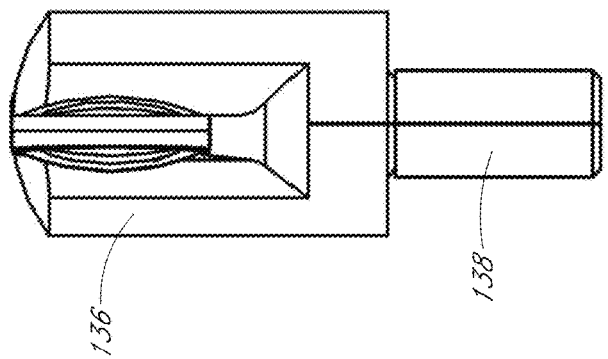
FIG. 5J illustrates a side view of the wing screw of FIG. 5I.
Figure 5I:
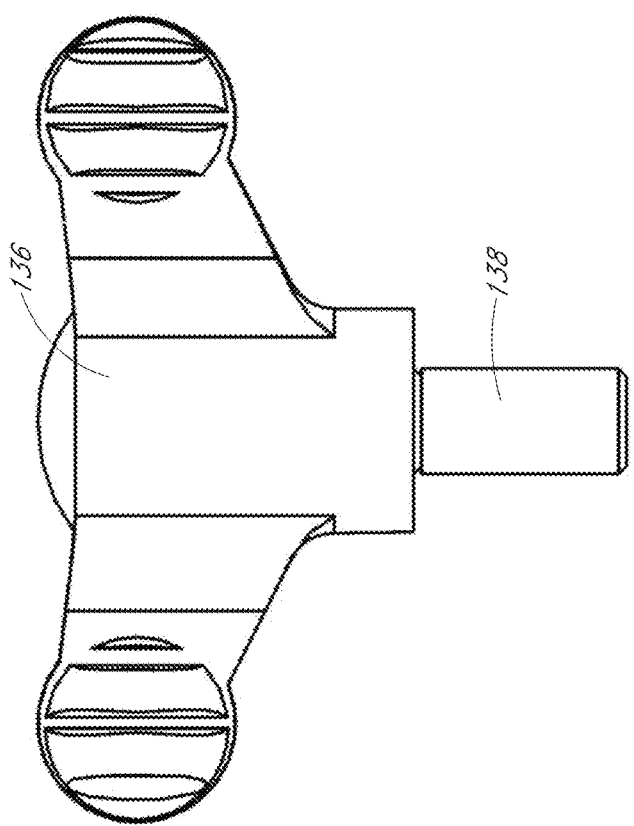
FIG. 5I illustrates a front view of an embodiment of a wing screw of a medical instrument support system.

FIGS. 5B-5J further illustrate components of the ball and socket joint and the clamp assembly 14. FIG. 5A illustrates a perspective view of the clamp assembly 14. FIGS. 5C, 5D, and 5E illustrate top, side, and front views, respectively, of a first portion of the clamp assembly 14. FIGS. 5F, 5G, and 5H illustrate front, side, and top views, respectively, of the shell 134 of the clamp assembly 14. FIGS. 5I and 5J illustrate front and side views, respectively, of the wing screw 136. These Figures illustrate additional features of the clamp assembly 14. The clamp assembly 14 further comprises a threaded hole 535 configured to accept a thread 138 of the wing screw 136. The shell 134 further comprises a hole 570 configured to allow the thread 138 of the wing screw 136 to pass therethrough and a flat 575 configured to allow clearance for the wing screw 136 as the wing screw 136 is rotated. The clamp assembly 14 further comprises a post 525 extending from the shell 132 and configured to be positioned within an opening 560 of the shell 134. The post 525 comprises a pin 530 configured to fit at least partially within grooves 565 of the shell 134 to form the pivot joint 510. The clamp assembly 14 also comprises an opening 545 and a threaded hole 540 opening into the opening 545 configured to allow the wing screw 126 to clamp the clamp assembly 14 to the frame 12. The wing screw 126 can in some embodiments be similar to or the same as the wing screw 136 shown in FIGS. 5I and 5J.

The embodiment of a medical instrument support system 10 shown in FIG. 2 further comprises chains 210 connected to the three removable threaded members. As shown in FIG. 2, a chain 210 connects the docking nut 62 to the docking member 60, the wing screw 136 to the main body of the ball clamp 56, and the wing screw 126 to the frame clamp 122. The chains 210 are advantageous for various reasons. For instance, the chains 210 can keep the removable members from falling to a floor during a medical procedure, causing the member to need to be re-sanitized. Additionally, the chains 210 can simplify assembly of the medical instrument support system 10 by keeping all removable components attached to the portion they are supposed to be installed to. The chains 210 can comprise, for example, stainless steel chains. In various other embodiments, the function of the chains 210 can be performed by other materials, such as a plastic or cloth string, a metal wire, and the like. Some embodiments do not utilize chains 210 or only utilize chains 210 for one or more components of the system.

Figure 6A:
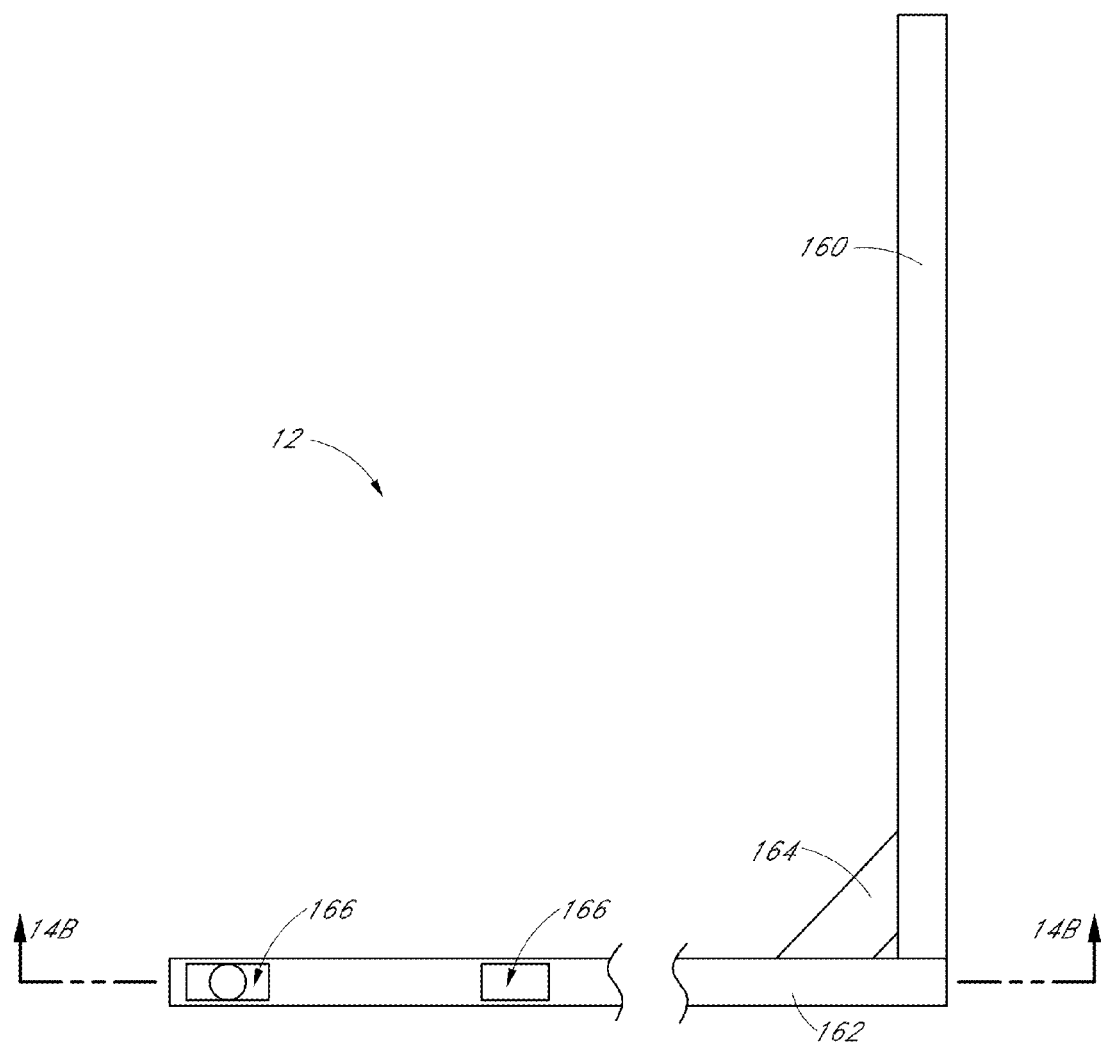
FIG. 6A illustrates a front view of an embodiment of an L-frame of a medical instrument support system.
Figure 6B:
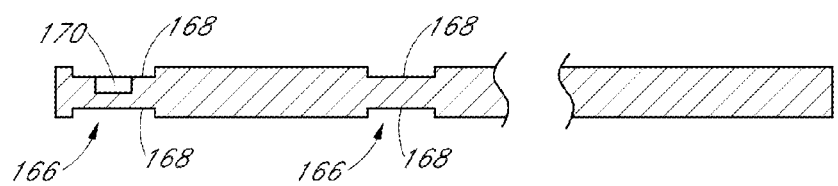
FIG. 6B illustrates a cross-sectional view of the L-Frame of FIG. 6A.

FIGS. 6A and 6B illustrate an embodiment of the frame or L-frame 12 of the medical instrument support system 10. FIG. 6A illustrates a front view of the L-frame 12. FIG. 6B illustrates a cross-sectional view of the L-Frame 12. The L-frame 12 comprises two steel rods 160 and 162 attached together at respective ends at approximately a 90° angle. A base plate 164 extends between the rods 164 and 162 adjacent an inside of the corner formed by the connected rods to increase a stability of the corner joint. Although the L-frame 12 comprises steel in this embodiment, the L-frame 12 may comprise various materials, such as stainless steel, polymer, medical grade materials, and the like. In some embodiments, the L-frame 12 is configured to be disassembled and/or collapsed to more easily fit the L-frame 12 components in, for example, an autoclave for sterilization.

In this embodiment, the rod 162 comprises two spaced apart attachment regions 166 to which respective clamp assemblies 14 can be attached. The rod 162 is of a generally circular cross section and each clamping region 166 comprises a pair of parallel diametrically opposed flat lands 168 machined into the rod 162. A blind hole 170 is formed in the land 168 of the attachment region 166 most distant the rod 160 to receive the thread shaft 128 of a wing screw 126. However, in other embodiments, a blind hole is formed (a) in the other or (b) both attachment regions 166. In some embodiments, no blind hole 170 is present. In various other embodiments, the L-frame 12 comprises other types of attachment regions 166, as long as a clamp assembly 14 is able to attach to the region 166, and the region 166 is able to react forces applied to the L-frame 12 by the clamp assembly 14.

In some embodiments, the MISS 10 may comprise two or more medical instrument holders 16, one of each coupled to respective attachment regions 166. One of the medical instrument holders may support an instrument such as an intra-uterine cannula, while the other can support an instrument such as rectal probe. Both these instruments are used simultaneously in various gynecological procedures. The instruments are coupled to respective medical instrument docking ports 22 at the end of each of the medical instrument holders 16. A laparoscopic camera can be supported on the same or another L-frame 12 (or differently shaped frame) by a medical instrument holder 16 provided with a docking member 60b and a camera holder 80, as shown in, for example, FIGS. 7 and 11A-11C. If the laparoscopic camera is supported on the same L-frame 12 as the intra uterine cannula and rectal probe, then an additional (third) attachment region 166 may be provided on L-frame 12. The additional attachment region may be on the rod 160 of the L-frame 12.

In various embodiments, the frame 12 can take various forms. For example, a frame can comprise one straight rod, instead of two rods forming an L-shape. A frame can additionally be shaped in any other manner sufficient to allow clamping one portion of the frame to a patient support and clamping a clamp assembly to another portion of the frame. Attachment regions 166 can additionally be positioned anywhere along the frame 12, and do not have to be parallel to each other.

Figure 8:
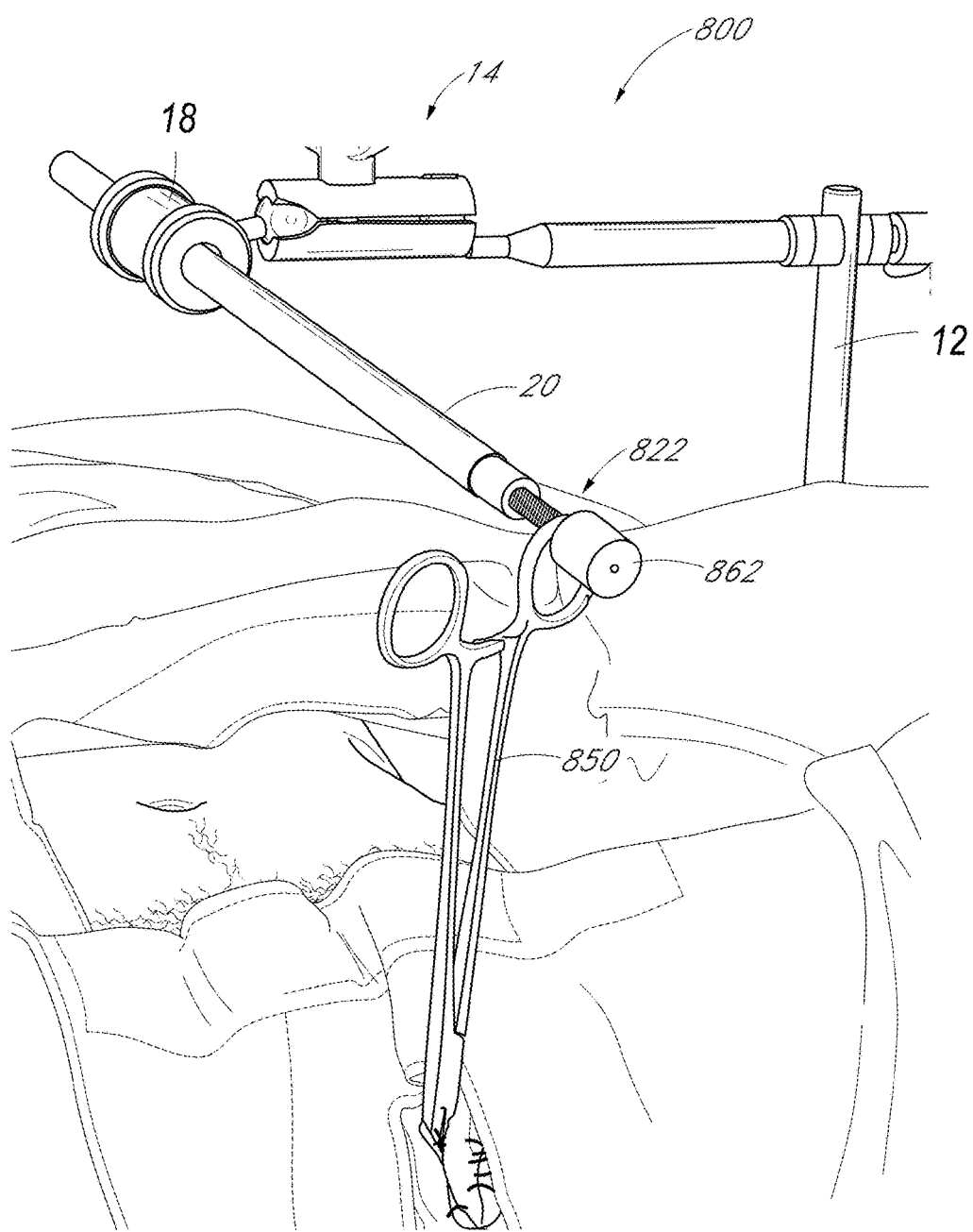
FIG. 8 illustrates an embodiment of a medical instrument support system supporting a tenaculum in use with a patient.

FIGS. 7 and 8 illustrate alternate embodiments of medical instrument support systems. FIG. 7 illustrates a medical instrument support system 700 supporting a medical instrument 750. In this embodiment, the medical instrument 750 is a laparoscopic camera. The medical instrument support system 700 illustrates that the frame 712 can be positioned to extend above a patient support and position the medical instrument support system 700 over the patient, as opposed to the medical instrument support system 10 shown in FIG. 1, which is positioned from underneath the patient. The medical instrument support system 700 comprises a docking port 722 further described and shown below in FIGS. 10A-10C. In this embodiment, the support rod 720 is similar to the support rod 20 of the medical instrument support system 10, except that the support rod 720 has a generally rectangular or square cross-section instead of a generally round cross-section. Additionally, the support coupling 18 is configured to accept a generally rectangular support rod 720 and to limit rotational motion of the support rod 720 along an axis of the support coupling 18. Details of this embodiment of a support coupling 18 are shown in FIGS. 9A and 9B.

The embodiment shown in FIG. 7 may be advantageous because the offset docking port 722 may introduce a relatively large rotational moment into the support rod 720. The relatively large rotational moment may, in some cases, be too large for the O-ring of the support coupling 18 to resist alone. Therefore, the combination of a noncircular support rod 720 and a support coupling 18 configured to accept a non-circular support rod allows a mechanical contact between the support rod 720 and support coupling 18 (as shown in FIGS. 9A and 9B) to further limit rotational motion of the support rod 720.

FIG. 8 illustrates a medical instrument support system 800 supporting a tenaculum in use with a patient. The medical instrument support system 800 is similar to the medical instrument support system 700 shown in FIG. 7, except the support coupling 18, support rod 20, and docking port 822 are of a different configuration. In this embodiment, the support coupling 18 and support rod 20 are similar to the support coupling and support rod shown in FIG. 2. However, the docking port 822 is of a different configuration. In this embodiment, the docking port 822 comprises a docking nut 862 threaded onto a threaded rod protruding from the support rod 20. The docking nut 862 and support rod 20 produce a recessed region between an end of the support rod and an end of the docking nut 862 where a handle of a medical instrument 850, for example, the tenaculum shown in FIG. 8, may be positioned and held in position.

Figure 9A:
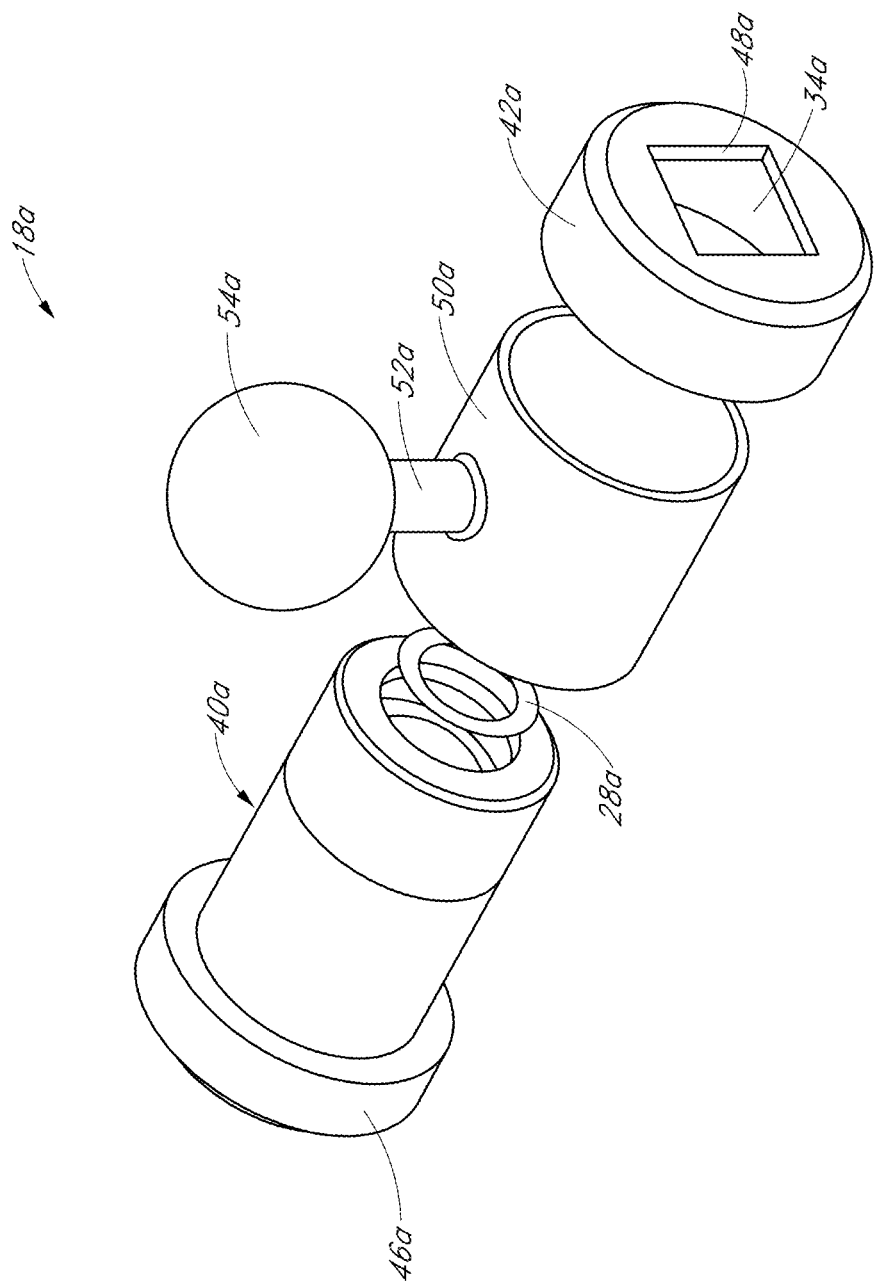
FIG. 9A illustrates an exploded view of an embodiment of a support coupling of a medical instrument support system.

FIGS. 9A-9C and 10A-10C illustrate in greater detail some of the components of the medical instrument support system 700 illustrated in FIG. 7. These figures illustrate that the medical instrument holder and its component parts, namely the support coupling 18, rod 20, and medical instrument docking port 22 may be formed in different configurations. For example FIGS. 9A-9C illustrate a medical instrument holder 16a with a support coupling 18a mounted on a rod 20a having a square cross sectional shape. In describing the medical instrument holder 16a the same reference numbers are used to denote the same or corresponding features of the medical instrument holder 16, but with the addition of the suffix "a". The support coupling 18a is formed with a modified first stop 42a having an aperture 48a in the shape of a square to closely fit over the square shaped rod 20a. In most other aspects the coupling 18a is the same as the coupling 18 as shown in FIGS. 4A-4D. By virtue of this arrangement, the coupling 18a provides only a single degree of freedom for the rod 20a, this being freedom to slide linearly. This form of medical instrument holder 16a may be used for example where it is desired to hold an instrument in a manner where it is unable to rotate about the rod 20a. As shown in FIG. 9C, the second end 36a of the axial through hole 26a in the support coupling 18a remains circular in shape and the rod 20a is in frictional contact with the O-ring 28. In some embodiments, however, the axial through hole 26a and/or the second end 36a may be rectangular in shape similar to the aperture 48a.

FIGS. 10A-10C illustrate a portion of a further form of medical instrument holder 16b. The embodiment shown in FIGS. 10A-10C can comprise the docking port 722 illustrated in FIG. 7. In particular, these figures depict a rod 20b, docking member 60b, and a camera holder 80 which is coupled to the rod 20b via the docking member 60b. Although not shown, the medical instrument holder 16b also comprises a support coupling 18a of the type shown in FIGS. 9A-9C. The rod 20b is of a square cross sectional shape and can be similar to the rod 20a as shown in FIGS. 9A-9C. However, one end of the rod 20b is provided a plug 82. Plug 82 can be configured to press fit into the end of rod 20b and is formed with a peripheral radially extending flange 84 and an axially extending threaded stub 86. An O-ring 88 can fit over the stub 86 and rest on the flange 84. The O-ring 88 can be advantageous to, for example, provide a friction force to keep the docking member 60b from rotating with respect to the rod 20b.

The docking member 60b is similar to docking member 60, but has some differences, including removal of the thread 72, and forming an internal thread in the hole 66b. The thread in the hole 66b is configured to engage the third stud 86. The hole 66b in this embodiment is a blind hole, but in an alternate embodiment it may be a through hole.

A link arm 90 is pivotally coupled to the docking member 60b via a pin 92 which passes through the hole 70 of docking member 60b and an end of the arm 90. This end of the arm 90 resides in channel 64b of member 60b. An opposite end of the arm 90 is formed with a radially extending flange 94 and an axially extending threaded stud 96. An O-ring 98 is fitted over stud 96 and sits on the flange 94.

The holder 80 is formed with arms 100 which extend axially from a base 102. An axially extending blind threaded hole (not shown) is formed in the base 102 for threaded engagement with the threaded stud 96. The O-rings 88 and 98 are elastically compressible and provide the user with the ability to vary the tension in the screw coupling between: the docking port 60b and the threaded stud 86; and, the camera holder 80 and the threaded stud 96. Also, the pivot coupling between the docking port 60b and the link arm 90 can be formed with a degree of stiffness so that the arm 90 can support itself when a camera or other instrument is held by the holder 80, such as is shown in FIG. 7. Although the embodiment shown in FIGS. 10A-10C utilizes a single pivot joint offset from a centerline of the rod 20b, various other embodiments may utilize more than one pivot joint and/or not include an offset from the centerline of the rod 20b.

Figure 11B:
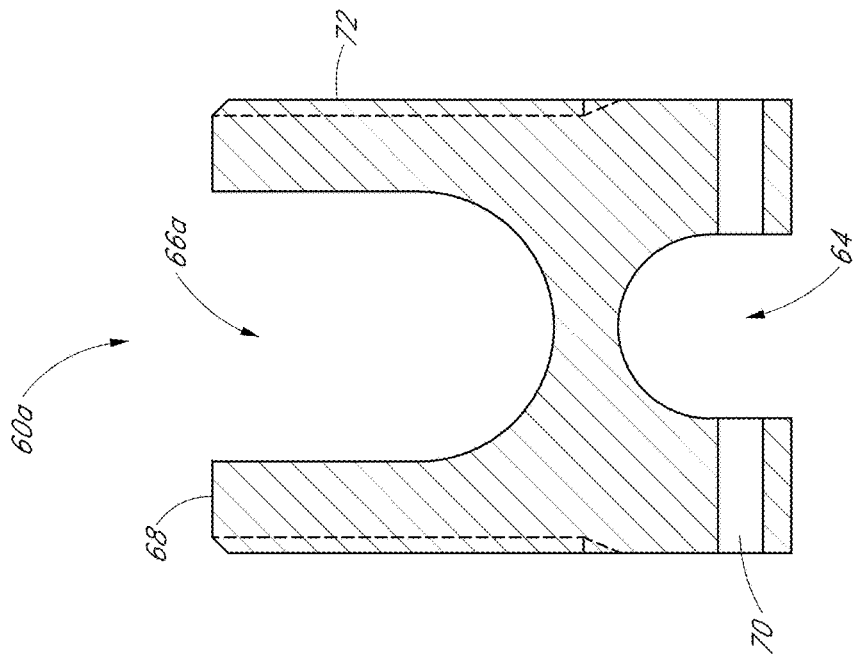
FIG. 11B illustrates a cross-sectional view of the docking member of FIG. 11A.
Figure 11A:
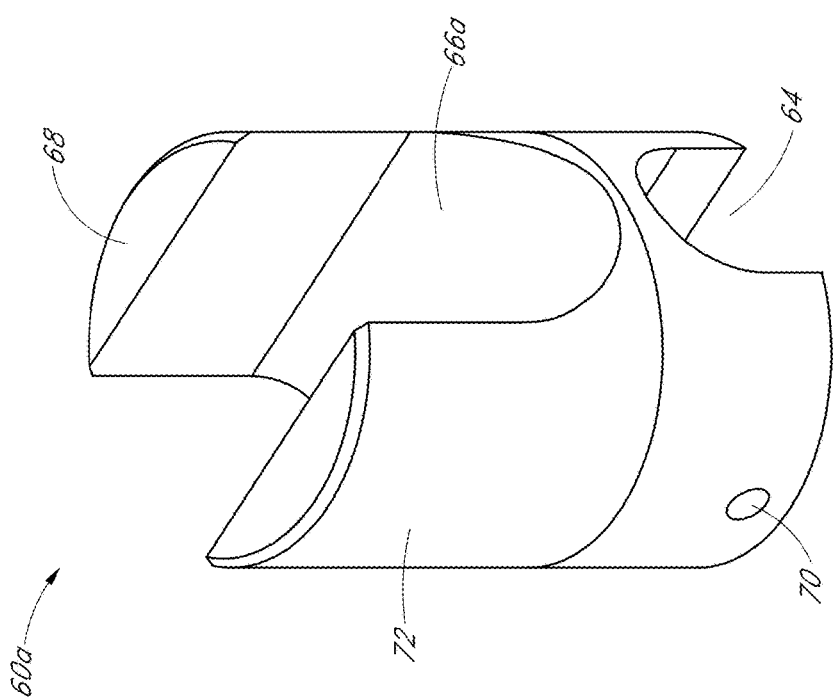
FIG. 11A illustrates a perspective view of an embodiment of a docking member of a medical instrument support system.

FIGS. 11A and 11B depict an alternate form of a docking member designated as docking member 60a. The docking member 60a differs from the docking member 60 by replacement of the hole 66 with a U-shape channel 66a. The provision of the channel 66a in place of the hole 66 enables the docking member 60a to accommodate medical instruments that cannot fit or otherwise be accommodated in the hole 66. A docking nut 62 similar to that shown in FIGS. 1A and 3C can be used with the docking member 60a to clamp a medical instrument in position.

FIGS. 12A and 12B illustrate an alternate embodiment of a docking port 1222. FIG. 12A illustrates a front view of the docking port 1222 and FIG. 12B illustrates a side view of the docking port 1222. The docking port 1222 is pivotally coupled to a support bar or rod 1220 through a pivot joint 1210. The support bar 1220 can be similar to the support rod 20 shown in FIG. 2. The support rod 1220, however, comprises a plug at one end to create the pivot joint 1210 for coupling to the docking port 1222. The pivot joint 1210 enables the docking port 1222 to have one degree of rotational freedom with respect to the support bar 1220. As with any other embodiment of a docking port described herein, the docking port 1222 may alternatively be coupled to a support rod using various other joints, such as a double-jointed pivot and/or a ball and socket joint, and may be inline or offset from a centerline of the support rod.

The docking port 1222 comprises a docking member 1260 having a channel 1266 for accepting a medical instrument. The docking port 1222 further comprises a clamping block 1262 configured to move relative to the docking member 1260 to enlarge or reduce the size of a space between the channel 1266 and a bottom surface of the clamping block 1262. The clamping block 1262 can be moved by rotating a twist handle 1215 attached to a screw 1225 engaged with the docking member 1260. In some embodiments, the docking port 1222 further comprises an anti-rotate bar 1230 to keep the clamping block 1262 aligned with the docking member 1260 as the twist handle 1215 is rotated. The docking port 1222 may be advantageous, for example, because various sized medical instruments can be accommodated within the opening between the channel 1266 and clamping block 1262.

Figure 13:
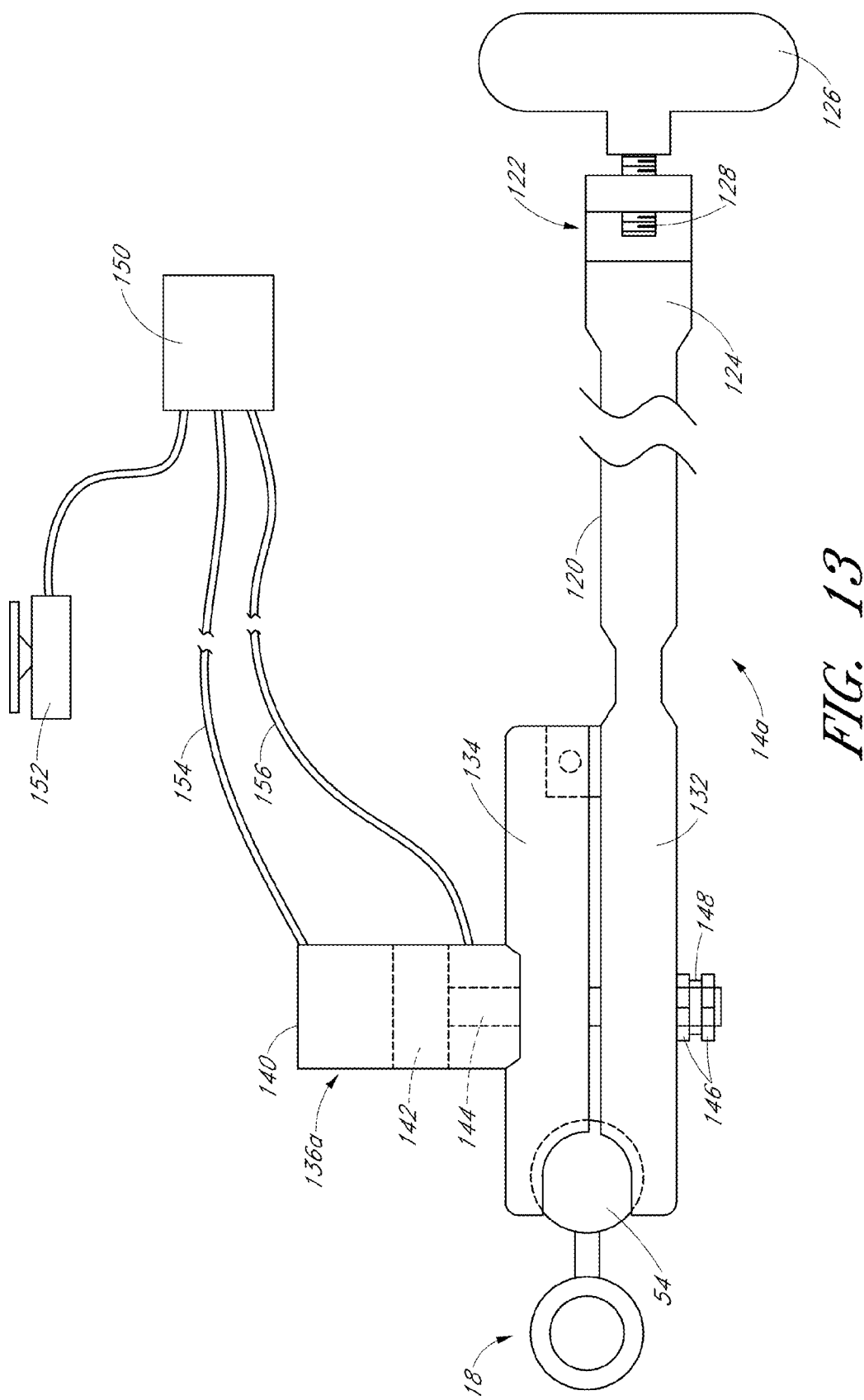
FIG. 13 illustrates a system diagram of a clamp assembly of a medical instrument support system having a powered actuator.

FIG. 13 depicts an alternate embodiment of a clamp assembly which is designated as 14a. All the features of the clamp assembly 14a which have the same or a similar function as those of the clamp assembly 14 are designated with the same reference numbers. The features which differ in structure but perform similar function as those of the clamp 14 are denoted with the same reference number but with the suffix "a". The clamp assembly 14a differs from the clamp assembly 14 by replacement of the wing screw 136 with a powered actuator 136a. The powered actuator 136a may for example comprise a hydraulic, pneumatic, or electrically operated piston or screw to enable clamping and releasing of the shells 132 and 134. In this specific embodiment, the actuator 136a comprises a hydraulic ram 140 provided with an internal slidable piston 142 with integral rod 144. The rod 144 passes through each of the shells 132 and 134 and is engaged at its distal end by lock nuts 146 and an intervening spring washer 148. A pump 150 is provided with a foot operated switch or pedal 152 which can be operated by, for example, a surgeon. Hydraulic lines 154 and 156 provide communication between the ram 140 and the pump 150 and enable the supply of hydraulic fluid to opposite sides of the piston 142 to cause the piston 142 to slide in opposite directions either releasing or applying compressive force to the ball 54. This provides a surgeon with a hands-free way to control the degree of force on the ball 54 and thus selectively change the amount of force required to manipulate the position of the corresponding engaged support coupling 18.

Now that embodiments to the present invention have been described in detail, it will be apparent to those skilled in the relevant arts that new modifications and variations may be made to the invention without departing from the basic concepts. For example, the support coupling 18 is described and depicted as comprising a body 24 with a separate sleeve 50 retained on the body 24. Sleeve 50 by virtue of the ball 54 enables attachment of the support coupling 18 to a clamp assembly 14. However, in an alternate configuration, the arm 52 and ball 54 can be formed integrally with the body 24 in which case sleeve 50 is not required. The described embodiments depict use of only a single O-ring 28 seated in the corresponding groove 32. However, multiple O-rings can be incorporated each into its own groove or seat 32. For example, in FIG. 4C, second seat of the same configuration as seat 32 can be formed inside the hole 66 near the opening 36 to receive a further O-ring. Further, the second stop 46 is depicted as being formed integrally with the body 24. However, this may be formed as a separate stop or cap similar to first stop 42 and screwed onto a further form of the body 24.

Also modifications and variations together with others or the obvious persons ordinarily skilled in the art are deemed to be within the scope of the present invention and the nature of which is to be determined by the description and in the claims.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

What is claimed is:

1. A repositionable medical instrument support system, the system comprising:
   a frame for rigidly connecting the system to a patient support;
   a ball and socket joint configured to provide three degrees of rotational freedom, the ball and socket joint comprising a ball member and an actuator, wherein the ball member is at least partially surrounded by a clamping member, wherein the clamping member is adjustable through a continuous range to vary a first friction force between the clamping member and the ball member, and wherein the actuator is configured to apply a variable actuating force to the clamping member to create the first friction force between the ball member and the clamping member;
   a frame mounting arm configured to mount the ball and socket joint to the frame;
   a sliding joint configured to provide one degree of translational freedom, the sliding joint comprising a support coupling and a support bar passing through the support coupling, wherein a resilient member positioned between the support coupling and support bar creates a second friction force between the support coupling and the support bar;
   a connecting arm configured to connect the sliding joint to the ball and socket joint; and
   a docking member configured to engage a medical instrument to support the medical instrument during a medical procedure, wherein the docking member comprises a base portion pivotally coupled to an end of the support bar and having a recess passing therethrough for receiving a portion of the medical instrument, wherein the docking member further comprises a docking nut engagable with the base portion to clamp the portion of the medical instrument received by the recess of the base portion, wherein the base portion comprises a screw thread engagable with a screw thread of the docking nut to enable clamping of the portion of the medical instrument received by the recess of the base portion,
   wherein the actuator is capable of setting the first friction force at a magnitude sufficient to resist a gravitational force applied by the medical instrument to the docking member, but that enables rotational movement of the ball member responsive to an externally applied force that overcomes the first friction force, and
   wherein the second friction force is sufficient to resist the gravitational force applied by the medical instrument to the docking member, but enables translational movement of the support bar through the support coupling responsive to an externally applied force that overcomes the second friction force.

2. The repositionable medical instrument support system of claim 1, wherein the sliding joint is additionally configured to provide one degree of rotational freedom between the support coupling and support bar.

3. The repositionable medical instrument support system of claim 1, wherein the sliding joint is configured to limit rotational movement of the support rod about an axis of the support coupling by engaging an outer surface of the support rod with a non-circular opening of the support coupling.

4. A repositionable medical instrument support system, the system comprising:
   a frame for rigidly connecting the system to a patient support;
   a ball and socket joint configured to provide three degrees of rotational freedom, the ball and socket joint comprising a ball member and an actuator, wherein the ball member is at least partially surrounded by a clamping member, wherein the clamping member is adjustable through a continuous range to vary a first friction force between the clamping member and the ball member, and wherein the actuator is configured to apply a variable actuating force to the clamping member to create the first friction force between the ball member and the clamping member;

a frame mounting arm configured to mount the ball and socket joint to the frame;

a sliding joint configured to provide one degree of translational freedom, the sliding joint comprising a support coupling and a support bar passing through the support coupling, wherein a resilient member positioned between the support coupling and support bar creates a second friction force between the support coupling and the support bar;

a connecting arm configured to connect the sliding joint to the ball and socket joint; and a docking member configured to engage a medical instrument to support the medical instrument during a medical procedure, wherein the actuator is capable of setting the first friction force at a magnitude sufficient to resist a gravitational force applied by the medical instrument to the docking member, but that enables rotational movement of the ball member responsive to an externally applied force that overcomes the first friction force, wherein the second friction force is sufficient to resist the gravitational force applied by the medical instrument to the docking member, but enables translational movement of the support bar through the support coupling responsive to an externally applied force that overcomes the second friction force, and wherein the at least one resilient member is configured to additionally create a rotational friction force between the support bar and the resilient member to enable the body to limit rotational motion of the support bar around the longitudinal axis until an external force is applied to the support bar that is of a magnitude sufficient to overcome the rotational friction force.

5. A method of supporting a medical instrument during a medical procedure using the repositionable medical instrument support system of claim 4, the method comprising:

connecting the frame of the medical instrument support system to the patient support;

engaging the medical instrument with the docking member of the medical instrument support system such that a reaction force is provided to the medical instrument from the docking member to oppose motion of the medical instrument, wherein the reaction force is transferred from the patient support through at least the ball and socket joint and sliding joint to the docking member; and positioning the medical instrument by overcoming at least one of the first friction force, the second friction force, or the rotational friction force.

6. The repositionable medical instrument support system of claim 4, wherein the patient support comprises a table.

7. The repositionable medical instrument support system of claim 4, wherein the frame mounting arm is configured to releasably mount the ball and socket joint to the frame.

8. The repositionable medical instrument support system of claim 4, wherein the first friction force and second friction force are of a magnitude that enables the support system to support the medical instrument during a medical procedure, but that also enables the medical instrument and support system to be repositioned by applying an external force to the support system that overcomes one or both of the first and second friction forces.

9. The repositionable medical instrument support system of claim 4, further comprising at least one additional sliding joint, at least one additional connecting arm, and at least one additional docking member coupled to the frame to enable simultaneous supporting of more than one medical instrument.

10. The repositionable medical instrument support system of claim 4, wherein the frame comprises at least two mounting locations, wherein the at least two mounting locations are each configured to accept a frame mounting arm and are positioned to allow at least two frame mounting arms to be simultaneously mounted to the frame.

11. The repositionable medical instrument support system of claim 10, wherein the at least two mounting locations comprise a flat configured to accept a clamp portion of the mounting arm.

12. The repositionable medical instrument support system of claim 4, wherein the first friction force is adjustable by turning a handle connected to a threaded member of the clamping member.

13. The repositionable medical instrument support system of claim 4, wherein the first friction force is adjustable by actuating the actuator connected to the clamping member.

14. The repositionable medical instrument support system of claim 4, wherein the actuator further comprises a handle configured to enable a human hand to rotate a threaded member of the clamping member.

* * * * *